United States Patent [19]

McMichael

[11] Patent Number: 5,694,950

[45] Date of Patent: Dec. 9, 1997

[54] METHOD AND SYSTEM FOR USE IN TREATING A PATIENT WITH IMMUNOSUPPRESANTS USING WHOLE BLOOD LEVEL CRITERIA TO PREVENT AN ADVERSE IMMUNE RESPONSE

[75] Inventor: John Patrick McMichael, Wexford, Pa.

[73] Assignee: J & W McMichael Software, Inc., Wexford, Pa.

[21] Appl. No.: 291,223

[22] Filed: Aug. 16, 1994

Related U.S. Application Data

[63] Continuation-in-part of Ser. No. 934,208, Aug. 21, 1992, Pat. No. 5,365,948.

[51] Int. Cl.$^6$ ............................................. A61B 17/00
[52] U.S. Cl. .................... 128/898; 364/413.01; 540/455
[58] Field of Search .... 128/897–8; 364/413.01–413.02; 540/455

[56] References Cited

U.S. PATENT DOCUMENTS

| | | |
|---|---|---|
| 4,839,822 | 6/1989 | Dormond et al. |
| 4,880,014 | 11/1989 | Zarowitz et al. |
| 5,019,974 | 5/1991 | Beckers et al. |
| 5,365,948 | 11/1994 | McMichael .......................... 128/898 |

OTHER PUBLICATIONS

Transplantation Proceedings, vol. XXIII, No. 6, Dec. 1991 (Appleton & Lange) (specifically, see the two articles below).

J. McMichael et al., Evaluation of a Novel "Intelligent" Dosing System for Optimizing FK 506 Therapy, Transplantation Proceedings, vol. XXIII No. 6, Dec. 1991, pp. 2780–2782.

G.J.V. Nossal, Summary of the First International FK 506 Congress: Perspectives and Prospects, Transplantation Proceedings, vol. XXIII No. 6, Dec. 1991, pp. 3371–3375.

Slides presented by John McMichael during a speech at the First International Congress on FK 506 on Aug. 21, 1991 at the University of Pittsburgh Medical Center (reported in the Transplantation Proceedings, vol. XXIII, No. 6, Dec. 1991).

Leslie Bendra Sabbagh, 'Intelligent' Dosing System Optimizes Drug Therapy, The Medical Post, Sep. 17, 1991, p. 26 (The Medical Post is published in Toronto, Ontario, Canada).

Abbottbase™ Aminoglycosides Demonstration Program Operations Manual, Version 2.00 (and Software (not included)), by Abbott Diagnostics, Aug. 1988.

*Primary Examiner*—John P. Lacyk
*Attorney, Agent, or Firm*—White & Case

[57] ABSTRACT

A method and system for use in treating a patient with an immunosuppressant to prevent an adverse immune response, either a rejection of a transplanted organ or an attack on the patient's body by its own immune system caused by an autoimmune disease, without unduly suppressing the ability of the patient's immune system to combat infection. The method employs an expert system to provide non-numerical information concerning the course of action to be taken with respect to a patient's immunosuppressant treatment, at a given time, including, in particular, an instruction on whether the immunosuppressant dosage being administered to the patient should be changed, and if so how. That instruction is determined by the expert system through analysis of standardized characterizations assigned to standardized patient examination criteria including levels of the immunosuppressant in blood plasma and whole blood. The method also employs a means for determining the actual numerical immunosuppressant dosage the patient should receive at a given time.

32 Claims, 15 Drawing Sheets

| | | No Change | | | | Increase | Decrease |
|---|---|---|---|---|---|---|---|
| Toxicity | None | X | X | X | X | X | |
| | Mild | X | | X | X | X | X |
| | Moderate | | | X | X | | X |
| | Severe | | | | | | X |
| Efficacy (Rejection/Desired Effect) | None | X | X | X | | | X |
| | Mild/Minimal | | | | | X | |
| | Moderate | | | | | X | |
| | Severe/Good | | | | | X | |
| Fk 506 whole Blood Level | High | | | | | | |
| | OK | X | | | | | |
| | Low | | X | X | X | | |
| Prednisone Dosage | High | | | | | | |
| | Low | | | | | X | |
| | Not on | | | | | X | |

FIG. 9

| | | No Change | Small Increase | Increase | Decrease | | |
|---|---|---|---|---|---|---|---|
| Toxicity | None | X | X | | | | |
| | Mild | X | X | | | X | |
| | Moderate | | X | | | X | |
| | Severe | | | X | | X | |
| Rejection | None | X | X | | | X | X |
| | Mild | | | | X | | |
| | Moderate | | | | X | | |
| | Severe | | | X | X | | |
| Fk 506 whole Blood Level | High | | | | | X | X | X |
| | OK | X | | | | | |
| | Low | X | X | | | X | | X |
| Creatinine Level | None | X | X | | | | |
| | Mild | X | | | | | X |
| | Moderate | | | | | | X |
| | Severe | | | | | | X |
| Bilirubin Level | High | | | | | | | X |
| | OK | X | X | | | | |
| Increase in SGot or SGPT Levels | Yes | | | | | | |
| | No | X | X | | | | |
| Prednisone Dosage | High | | X | | | | |
| | Low | | X | | | | |
| | Not on | | | | | | |

FIG. 10

| | | Severe | Moderate | Mild | Mild to Moderate | None to Mild | None |
|---|---|---|---|---|---|---|---|
| Tingling | Severe | | | X | | | |
| | Moderate | | | | X | | |
| | Mild | | | | | X | |
| | None | | | | | | X |
| Tremors | Severe | | | X | | | |
| | Moderate | | | | X | | |
| | Mild | | | | | X | |
| | None | | | | | | X |
| Sleep | Severe | | | X | | | |
| | Moderate | | | | X | | |
| | Mild | | | | | X | |
| | None | | | | | | X |
| Diabeto-gencity | Insulin required | X | | | | | |
| | Oral Agents | | X | | | | |
| | Elevated Glucose Levels | | | | X | | |
| | Normal Glucose Levels | | | | | | X |
| Nephro-toxicity | Sharp Increase in CR | X | | | | | |
| | Steady Rise in CR | | X | | | | |
| | Slight Rise in CR | | | | X | | |
| | None | | | | | | X |

FIG. 11

| Efficacy (Rejection/Desired Effect) | | Decrease | Increase Bolus of Steroid and Recycle | Increase Recycle to a Higher Dose | Increase Increase Maintenance | Prednisone Not on |
|---|---|---|---|---|---|---|
| | None | X | | | | |
| | Mild/Minimal | X | | | | |
| | Moderate | | X | X | | |
| | Severe/Good | | | X | X | |
| Prednisone Dosage | High | X | | | | |
| | Low | X | | | | |
| | Not on | | | | | X |

FIG. 12

METHOD AND SYSTEM FOR USE IN TREATING A PATIENT WITH IMMUNOSUPPRESANTS USING WHOLE BLOOD LEVEL CRITERIA TO PREVENT AN ADVERSE IMMUNE RESPONSE

CROSS REFERENCE TO RELATED APPLICATION

This application is a continuation-in-part ("CIP") of U.S. patent application Ser. No. 07/934,208, filed Aug. 21, 1992, now U.S. Pat. No. 5,365,948, and entitled "Method and System for Use In Treating A Patient With FK 506 To Prevent an Adverse Immune Response."

A portion of the disclosure of this patent document contains material which is the subject of copyright protection. The copyright owner has no objection to the facsimile reproduction by anyone of the patent disclosure as it appears in the public patent files of the United States Patent and Trademark Office, but otherwise reserves all other rights in the copyrighted material.

REFERENCE TO THE MICROFICHE APPENDIX

Reference is hereby made to a microfiche appendix submitted herewith in accordance with 37 CFR 1.96(b). The appendix contains the source code listing for 12 computer programs on a 2 microfiche having a total of 122 frames.

1. Field of the Invention

The present invention relates to a method and system for use in treating a patient to prevent an adverse immune response. In particular, this invention relates to a method and system for use in treating a patient with an immunosuppressant, specifically, either FK 506, Cyclosporin (CyA) or Rapamycin (RPM) to prevent either a rejection of a transplanted organ or an attack on the patient's body by its own immune system caused by an autoimmune disease, without unduly suppressing the ability of the patient's immune system to combat infection. The present invention utilizes the level of the immunosuppressant, i.e., the FK 506 level, or Cyclosporin or Rapamycin, in the whole blood of the patient as one of the parameters in the determination of the correct treatment of the patient with the immunosuppressant.

2. Background of the Invention

Once a patient has undergone an organ transplant, it is crucial that the patient's immune system be partially disabled so that it will not reject the allograft. The immune system must be disabled enough to prevent the body from rejecting the graft, i.e., mounting an adverse immune response, but not so much that the immune system will not be able to defend against viruses, bacteria or other infection. This balance must continue throughout the remainder of the patient's life to assure that neither rejection nor undue susceptibility to infection will occur.

One immunosuppressant drug utilized in the prior art for partial disablement of the body's immune system is Cyclosporin A ("CyA, Cyclosporin, or Cyclosporine"). Cyclosporin has been shown to be effective in targeting and partially disabling T cells, which are responsible for fighting off alien tissue, thus allowing for more successful transplants. Cyclosporin, however, tends to inflict damage on various organs due to its high potency. In order to ameliorate the harsh effects of Cyclosporin, the dosage of Cyclosporin administered to a patient in the prior art is minimized, and each dose is supplemented with dosages of other drugs such as steroids.

Another immunosuppressant utilized in the treatment of transplant patients is Rapamycin (RPM). As with Cyclosporin, RPM is a medication which can inflict damage on various organs and thus must be administered in a minimized dose, often accompanied with supplemental drugs such as steroids.

FK 506, which is 100 times more potent than Cyclosporin in inhibiting lymphocyte proliferation in mixed lymphocyte cultures, can be used as an immunosuppressant in place of Cyclosporin to prevent rejection of organ transplants. FK 506, a macrolide antibiotic produced by the fungus *Streptyces tsukubaenis*, has clinically been found to have a potent and targeted effect on T cells without the severe range of side effects exhibited by the similar use of the drug Cyclosporin. In addition, the use of FK 506 rather than Cyclosporin has been shown to lessen and even eliminate the need for the continued use of steroids. This, in turn, results in reduced instances of hypertension in transplant patients. R. Venkataramanan et al., Pharmacokinetics of FK 506 in Transplant Patients, *Transplantation Proceedings*, p. 2736 (December 1991).

Cyclosporin, RPM and FK 506 have also been found to be successful with patients afflicted with autoimmune diseases. As in the case of transplant patients, Cyclosporin, RPM and FK 506 inhibit the patient's T cells, prohibiting them from attacking the patient's own body, i.e., mounting an adverse immune response. Autoimmune diseases include, inter alia, multiple sclerosis, diabetes, psoriasis and rheumatoid arthritis.

There is a large inter-individual variability in the pharmacokinetics of many immunosuppressants including Cyclosporin, RPM and FK 506. R. Venkataramanan et al., Pharmacokinetics of FK 506 in Transplant Patients, *Transplantation Proceedings*, pg 2736 (December 1991). See also V. S. Warty et al., Practical Aspects of FK 506 Analysis (Pittsburgh Experience), *Transplantation Proceedings*, pg 2730 (December 1991); G. J. V. Nossal, Summary on the First International FK 506 Congress: Perspective and Prospects, *Transplantation Proceedings*, pg 3373 (December 1991). Thus, what may be an appropriate course of action with one patient may not be the appropriate course of action with another patient. Therefore, prior to the present invention, a physician needed to do a substantial amount of experimentation with Cyclosporin or FK 506 on a patent before the physician was in a position to know what course of action to take with respect to treating that patient with these pharmaceutical compounds.

The study and development of artificial intelligence ("AI") has recently provided a means for simulating the human decisional processes and has developed to a point where it can now be used in certain situations to solve problems and yield much the same results as human beings would. Thus, AI can help reduce the learning curve associated with acquiring knowledge in a particular area, including drug treatment.

An expert system is an application of AI designed to solve problems through the manipulation of data. Expert systems typically include a knowledge base of data and rules relating that data to additional data which is fed into the expert system for purposes of determining the solution to a problem.

Expert systems have recently found use in a variety of applications, such as agriculture, chemistry, computer design, construction, engineering, finance, management, health care and manufacturing. Moreover, prior art expert systems have been designed to address a relatively wide range of health care concerns. See Dormond et al., U.S. Pat. No. 4,839,822.

Beckers et al., U.S. Pat. No. 5,019,974, discloses a computerized system for diabetes management which gathers, processes and analyzes data to provide an outpatient with a personalized tailored treatment or medication program. Dormond et al., U.S. Pat. No. 4,839,822, discloses an expert system for use in treating various types of trauma.

In U.S. patent application Ser. No. 07/934,208, hereby incorporated by reference, the inventor of the present invention disclosed a method and system for the treatment of patients with FK 506. The method and system disclosed in that application relies on the use of blood plasma levels to determine as input to the expert system claimed therein.

At the present time, in the literature, whole blood is the monitoring matrix of choice for all immunosuppressants. Although there is no clear rationale for this, however, the general feeling is that whole blood provides a better representation of the drug level in the blood. From a technical point of view, there is some question regarding this reasoning. When the level of a certain compound in blood plasma is measured the assay measures the actual or absolute amount of the compound in the sample. In contrast, when whole blood is used, an isopropyl alcohol extraction is done on the whole blood sample and it is the alcohol extract that is assayed. The proportion of the drug that is extracted may not be constant and 100% of the drug is not extracted.

Doctors and researchers began using whole blood monitoring techniques due to a lack of a clear relationship between plasma levels and immunosuppressant dosages. The use of whole blood monitoring has grown to the point where the use of blood plasma levels in the expert system and method of treating patients required modification in order to work with this type of whole-blood based information. The present invention provides, therefore, the physician with the ability to use whole blood levels of the immunosuppressants in the treatment of patients.

Due to their potency, an overdose of Cyclosporin, RPM or FK 506 can fatally cripple the immune system's ability to defend against bacteria and viruses. An under-dose, on the other hand, can result in an adverse immune response in a patient who has received a transplanted organ or is affected with an autoimmune disease. It is, therefore, critical that a patient who requires Cyclosporin, RPM or FK 506 be given the proper dosage so as to balance these harms and that therapeutic monitoring occur. See J. McMichael, Evaluation of A Novel "Intelligent" Dosing System For Optimizing FK-506 Therapy, *Transplantation Proceedings*, p. 2780 (December 1991).

Determining the proper Cyclosporin, RPM or FK 506 dosage to be administered to a patient generally is complicated by the inter-individual variability in the pharmacokinetics of immunosuppressants such as Cyclosporin and FK 506. Moreover, the amount a given patient needs changes over time depending on how close the patient is to being stable. A patient is considered stable when he or she no longer exhibits the effects of receiving too much Cyclosporin, RPM or FK 506, known as toxicity (in particular, nephrotoxicity), and displays no rejection or autoimmune disease flare ups.

None of the prior art methods for dosing patients is capable of handling these variables. Thus, none of them can be used to determine the proper immunosuppressant dosage to be administered to a patient at a given time. Linear equations based on population parameters such as age, weight or sex assume that people respond to a particular drug in accordance with their population characteristics. That assumption, and those types of equations, fail to account for variability among people within the same population parameters. McMichael, J., H. Doyle, R. Liberman, S. Mitchell, L. Dvorchik, J. McCauley, J. Fung and J. Starzl, *Three Dimensional Response Surface Comparison of FK 506 and Cyclosporine, Proceedings:* 1994 *SCS Western Multiconference,* Simulation in the Health Sciences, (ed) Anderson and Katzper, pp. 143–148 (1994).

Non-linear least squares modeling methods cannot be used either. Those methods involve use of a vast amount of data concerning the general population as a whole to arrive at a solution. The larger the quantity of data, the better the fit. Not only do those types of methods involve the use of unnecessary criteria, but moreover, like linear equations, they fail to account for variability among people within the same population parameters.

Bayesian analysis is also inappropriate for determining proper Cyclosporin, RPM and FK 506 dosages. Unlike linear equations and non-linear least squares methods, Bayesian analysis does employ specific data about the medical status of a particular patient. However, the analysis also requires results from previous dosing experiences with the general population. As already mentioned, relying on the general public to determine the appropriate dosage of Cyclosporin, RPM or FK 506 for a particular patient is inappropriate because of the inter-individual variability in the pharmacokinetics of Cyclosporin, RPM and FK 506. Moreover, Bayesian analysis's ability to determine a proper dosage becomes reliable only after treating a patient with a particular drug for a significant period of time. Thus, it cannot be used to accurately predict proper dosages during the early dosing periods of a drug, especially Cyclosporin, RPM and FK 506.

Pharmacokinetics compartment modeling is not a viable way of dosing a patient with Cyclosporin, RPM or FK 506 either. Jain, A. B. R. Venkataramanan, J. Fung, J. Burckart, J. Emeigh, W. Diven, V. Warty, K. Abu-Elmagd, S. Todo, M. Alessiani and T. E. Starzl, Pharmacokinetics of Cyclosporine and Nephrotoxicity in Orthotopic Liver Transplant Patients Rescued With FK506, *Transplantation Proceedings*, 23(6), pp.2777–2779 (1991). While R. Venkataramanan (in his paper entitled Pharmacokinetics of FK 506 in Transplant Patients published in the *Transplantation Proceedings* in December of 1991 at page 2736) has suggested that a two compartment model could be employed, a subsequent experiment, which utilized such a model for dosing FK 506, shows that compartment modeling will not work.

The problem with pharmacokinetics compartment modeling is that the model comes from a standardized equation which is modelled upon the general population's interaction with a particular drug. It, therefore, fails, once again, to take into account inter-individual variability. An example of a one-compartment pharmacokinetics model for dosing aminoglycosides can be found in Abbott Diagnostics' Aminoglycosides dosing computer program and instruction manual published in 1988. An example of an expert system which uses pharmacokinetics compartment modeling is U.S. Pat. No. 4,888,014, Zarowitz et al.

Another method presently available for determining immunosuppressant dosages is the trial-and-error method. That is, a patient could be given incremental dosages of Cyclosporin, RPM or FK 506, and the patient's reaction thereto could be observed and used to determine the frequency and quantity of subsequent dosages. The risks of a trial-and-error methodology of prescribing Cyclosporin, RPM and FK 506 are, however, evident. An overdose would be extremely difficult to avoid and, as mentioned before, could cripple the immune system's ability to defend against bacteria and viruses. An under-dose could result in rejection or a relapse of an autoimmune disorder.

DISCLOSURE OF THE INVENTION

The present invention is a method and system for use in treating a patient with the immunosuppressant pharmaceutical Cyclosporin, RPM and FK 506 to prevent an adverse immune response by partially suppressing the patient's immune system without unduly suppressing the ability of the immune system to combat infection. One embodiment of the present invention includes use of an expert system to provide information about the course of action a physician should take in treating a patient with Cyclosporin, RPM or FK 506, including a non-numerical instruction pertaining to the next dosage of Cyclosporin, RPM or FK 506 that a patient should be administered. The non-numerical instruction providing embodiment involves the following steps.

First, an initial examination of the patient is made to determine the status of particular criteria, e.g., the patient's creatinine level and blood glucose level. Next, an initial dose of Cyclosporin, RPM or FK 506 administered to the patient. The dosage contained in the initial dose, and how it is administered, depends upon the medical condition being treated.

After a predetermined time, typically one day, the patient is examined again to determine the degree, if any, of toxicity the patient is experiencing from the immunosuppressant; the efficacy of the immunosuppressant treatment in preventing an adverse immune response; and the current level of Cyclosporin, RPM or FK 506 in the patient's whole blood, not blood plasma. The examination may also include a determination of other criteria, if necessary, for determining the appropriate course of action. For example, a patient who has received a transplanted liver will also be examined to determine his or her creatinine level, bilirubin level, and SGOT and SGPT levels, and possibly, alkaline phosphatase level and whether there are mechanical problems.

Once the second examination is complete, each of the patient examination criteria is assigned a characterization from a range of predetermined standardized characterizations. Each patient examination criterion has its own range of predetermined standardized characterizations. The characterization assigned to each of the patient examination criteria is then delivered to an expert system which processes those characterizations to provide at least one non-numerical instruction pertaining to a patient's next Cyclosporin, RPM or FK 506 dosage.

The expert system includes a general purpose computer comprising an input means, an output means, a data storage means and a processor. The data storage means contains a knowledge base and an expert computer program. The knowledge base includes rules which designate one of a plurality of next Cyclosporin, RPM or FK 506 dosage instructions to every possible combination of the characterizations which can be assigned to the patient examination criteria. The expert computer program receives the characterization assigned to each of the patient examination criteria and then searches through the rules in the knowledge base to find a rule which covers the assigned characterizations, and thereby determines the appropriate next Cyclosporin, RPM or FK 506 instruction.

Once a rule is found, the expert system outputs the next Cyclosporin, RPM or FK 506 instruction. The physician then administers a next dose of Cyclosporin, RPM or FK 506 to the patient in accordance with the next Cyclosporin, RPM or FK 506 instruction provided by the expert system.

Three other embodiments of the present invention involve determining the exact numerical dosage of Cyclosporin, RPM or FK 506 to be administered to a patient at a given time during the Cyclosporin, RPM or FK 506 treatment process. However, the second of these three additional embodiments is only able to determine the next immunosuppressant dosage when the next dosage is being decreased with respect to the current dosage. These additional embodiments involve the following steps.

All three of these embodiments begin with an initial dose of Cyclosporin, RPM or FK 506 being administered to the patient. Next, the patient is examined to determine his or her current Cyclosporin, RPM or FK 506 whole blood level. At this point in the process, each of these three additional embodiments take parallel, but different, courses to determine the next dosage of the respective immunosuppressant which should be administered to the patient.

The first of these three embodiments requires that the physician determine the quantitative value which he or she wants the patient's Cyclosporin, RPM or FK 506 whole blood level to be in the immediate future. That value, which is referred to as the desired Cyclosporin, RPM or FK 506 whole blood level for the patient, and the values for the patient's current Cyclosporin, RPM or FK 506 dosage and current Cyclosporin, RPM and FK 506 whole blood level are then employed with the following relationships to obtain the next Cyclosporin, RPM or FK 506 dosage:

For Cyclosporin (CyA):

$$ND = CD - (((((CL-DL)/CL)/(2.5+(CD/1500) \times 2.5))/CD) + ((0.2 \times CD) \times (((1+d)-(1+e))/abs((1+d)))))$$

wherein,

ND=the next CyA dosage,
CD=the patient's current CyA dosage,
CL=the patient's current CyA whole blood level,
DL=the desired CyA whole blood level for the patient,
RD=the patient's previous CyA whole blood level,
e=CL−RD, and
d=DL−RD.

For FK 506:

$$ND = CD - (((((CL-DL)/CL)/(1+(CD/40)))/CD) + ((0.2 \times CD) \times (((1+d)-(1+e))/abs((1+d)))))$$

wherein

ND=the next FK 506 dosage,
CD=the patient's current FK 506 dosage,
CL=the patient's current FK 506 whole blood level,
DL=the desired FK 506 whole blood level for the patient,
RD=the patient's previous FK 506 whole blood level,
e=CL−RD, and
d=DL−RD.

For RPM:

$$ND = CD - (((((CL-DL)/CL)/(1+(CD/30)))/CD) + ((0.2 \times CD) \times (((1+d)-(1+e))/abs((1+d)))))$$ wherein, ND=the next RPM dosage,
CD=the patient's current RPM dosage,
CL=the patient's current RPM whole blood level,
DL=the desired RPM whole blood level for the patient, RD=the patient's previous RPM whole blood level
c=CL−RD
d=DL−RD The second of these embodiments (i.e., the embodiment which can only be used when the next immunosuppressant dosage is decreased with respect to the current dosage) somewhat parallels the non-numerical instruction providing embodiment discussed above. It requires that a physician assign a characterization to the patient's current Cyclosporin, RPM or FK 506 whole blood level. Then that characterization and the value for the patient's current Cyclosporin, RPM or FK 506 dosage are delivered to an expert system which processes that data to provide the next Cyclosporin, RPM or FK 506 dosage.

The expert system of the second embodiment contains the same general elements as the expert system of the non-numerical instruction providing embodiment and functions in a similar manner. Its knowledge base is different, however, in that it includes rules which designate a next Cyclosporin, RPM or FK 506 dosage (which is less than the current Cyclosporin, RPM or FK 506 dosage) to every possible combination of the characterizations which can be assigned to the patient's current Cyclosporin, RPM or FK 506 whole blood level and values for the patient's current Cyclosporin, RPM or FK 506 dosage. The expert computer program of the second embodiment searches through the rules to find one that covers the input data, and thereby determines the next Cyclosporin, RPM or FK 506 dosage.

The third embodiment combines aspects of the other two embodiments. Like the first embodiments, it requires that the physician determine the desired Cyclosporin, RPM or FK 506 level for the patient. Thereafter, the patient's current Cyclosporin, RPM or FK 506 dosage, the patient's current Cyclosporin, RPM or FK 506 whole blood level and the desired Cyclosporin, RPM or FK 506 level for the patient are entered into an expert system like the one described with respect to the second additional embodiment. The knowledge base of the expert system of the third embodiment includes rules which designate a next Cyclosporin, RPM or FK 506 dosage to every possible combination of values for the current Cyclosporin, RPM or FK 506 dosage, current Cyclosporin, RPM or FK 506 whole blood level and desired Cyclosporin, RPM or FK 506 level. The expert computer program of the third additional embodiment searches through the rules to find one that covers the input data, and thereby determines the next Cyclosporin, RPM or FK 506 dosage.

Each of these three additional embodiments includes the final step of administering a next dose of Cyclosporin, RPM or FK 506 to the patient in accordance with the dosage determined by the method employed.

The embodiment which provides the non-numerical instruction can be combined with each of the three embodiments which provide actual numerical dosages as well as combinations thereof. In addition, several of the steps of several of these embodiments can be and should be repeated in a systematic manner throughout the patient's life. Finally, the method of the present invention can also be used to treat a patient with other immunosuppressant agents, such as prednisone, along with Cyclosporin, RPM or FK 506. In such situations, depending upon the embodiment employed, the method of the present invention can provide a non-numerical instruction concerning the course of action the physician should take with respect to such immunosuppressant agent, and, in some instances, the numerical next dosage for that other immunosuppressant agents as well.

BRIEF DESCRIPTION OF THE DRAWINGS

For the purpose of illustrating the present invention, the drawings show several embodiments of the present invention; it being understood, however, that this invention is not limited to the precise arrangements shown.

FIGS. 9, 10, 11, and 12 are charts containing rules which are used by the present invention.

DETAILED DESCRIPTION OF THE INVENTION

The method of the present invention for use in treating a patient with immunosuppressants such as Cyclosporin, Rapamycin ("RPM") or FK 506 using the patient's whole blood levels of the immunosuppressant—to prevent an adverse immune response by partially suppressing the patient's immune system without unduly suppressing the ability of the immune system to combat infection—can be implemented in several different embodiments, many of which employ the same or similar steps. For simplification purposes, the manner in which several of those embodiments can be implemented is now described separately.

Figure 1:
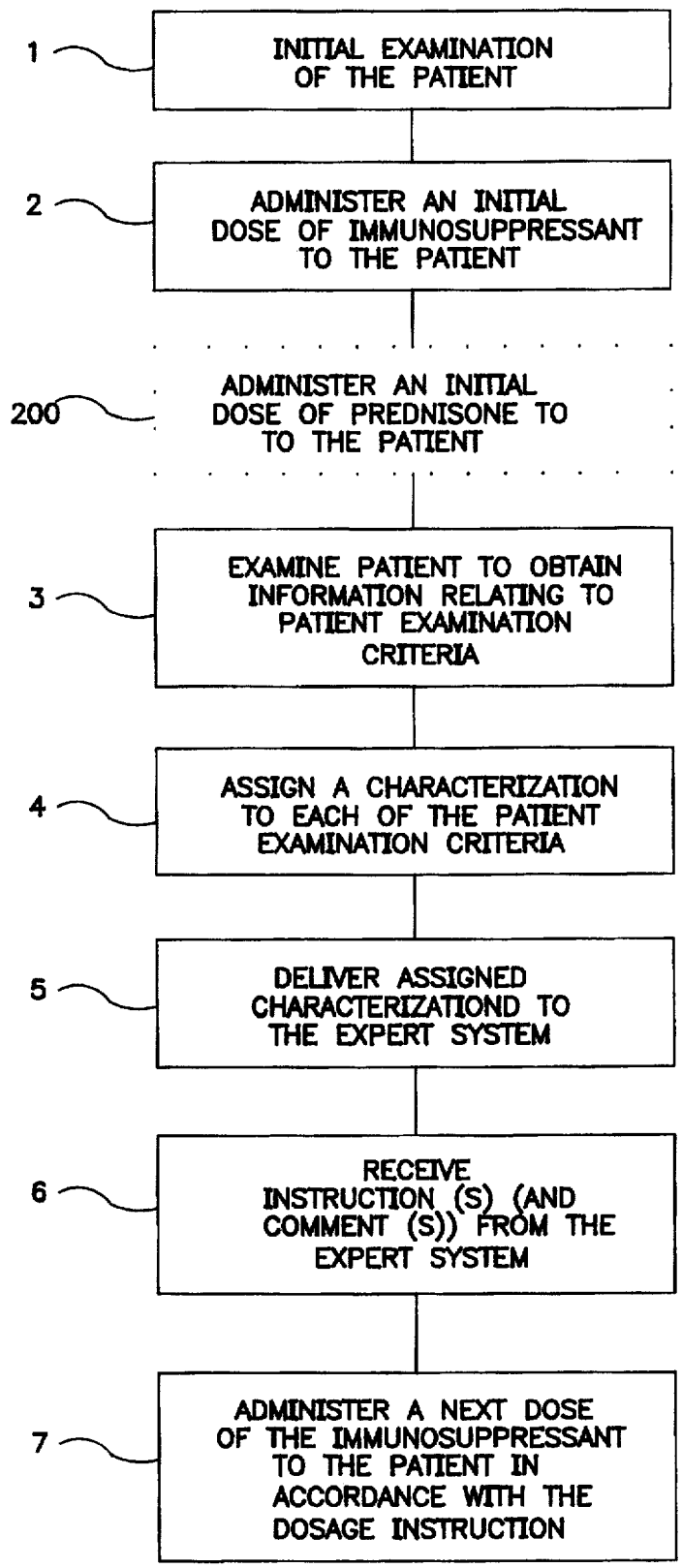
FIG. 1 is a flow chart depicting a first embodiment of the present invention.

One embodiment of the present invention utilizes an expert system to provide information about the course of action a physician should take in treating a patient with Cyclosporin, RPM or FK 506. Referring to FIG. 1, this embodiment begins its process with an initial examination of the patient, step 1 of FIG. 1. The initial examination is used to determine the patient's creatinine level and blood glucose level (i.e., blood sugar level) for comparison purposes later in the process.

Figure 2:
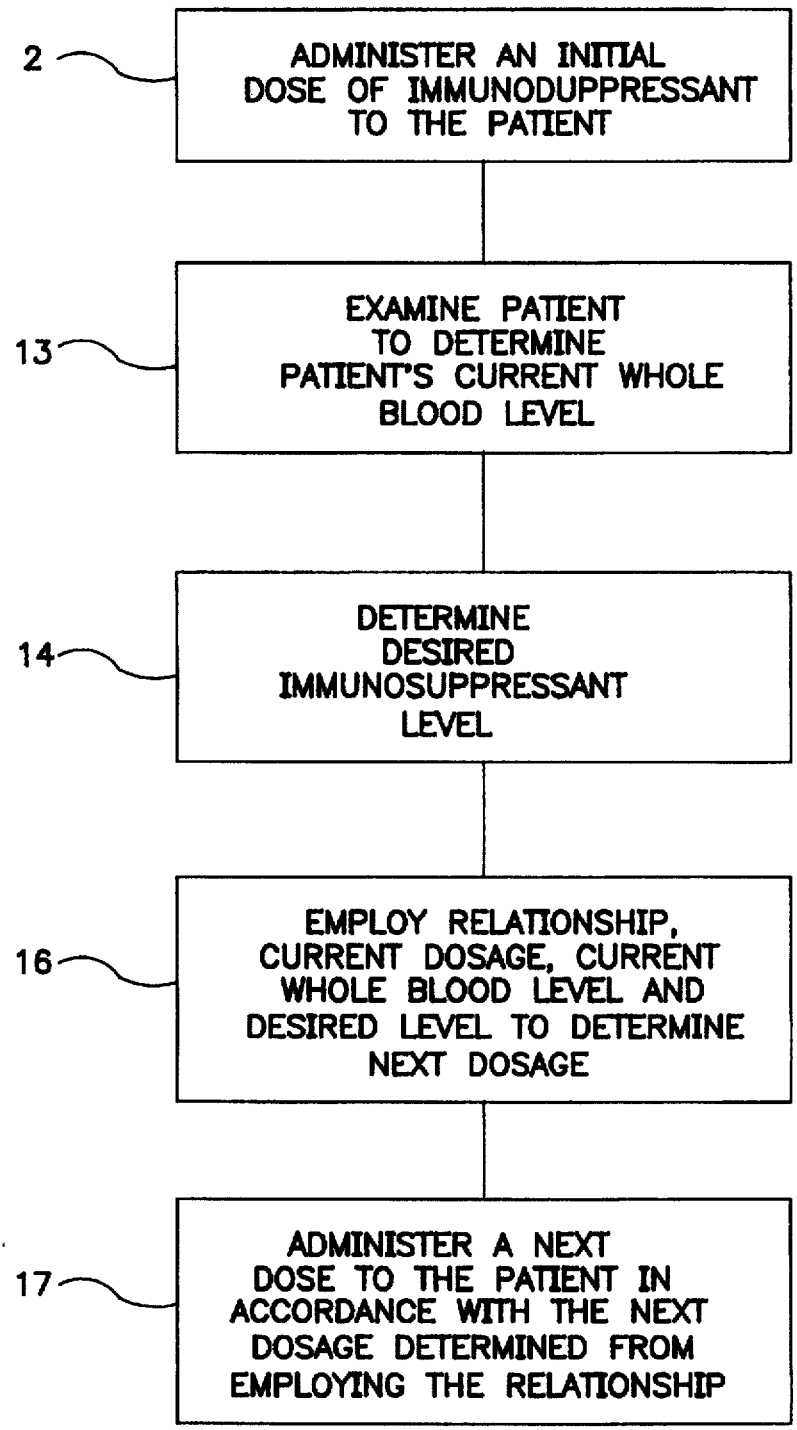
FIG. 2 is a flow chart depicting a second embodiment of the present invention.

Once the initial examination is completed, an initial dose of Cyclosporin, RPM or FK 506 is administered to the patient, step 2 of FIG. 2. In the preferred embodiment, the patient has not previously received any Cyclosporin, RPM or FK 506, and administration of the initial dose of Cyclosporin, RPM or FK 506 will be the patient's first dose of that immunosuppressant drug.

The dosage administered to a patient in the initial dose depends upon whether the patient is an organ transplant patient or a patient affected with an autoimmune disease. Which of these two medical conditions is being treated will also have an impact, in the preferred embodiment, on the manner in which the initial dose is administered to the patient.

If the patient is an organ transplant patient, the initial dose should preferably consist of a dosage of 5 milligrams of Cyclosporin, 0.05 milligrams of RPM or 0.15 milligrams of FK 506 for each kilogram of the patient's body weight. In the preferred embodiment, the initial dose of Cyclosporin, RPM or FK 506 provided to an organ transplant patient is administered intravenously. If, however, the organ transplant patient's gastrointestinal tract is functional, then the initial dose can be administered orally, in which case, the dosage should be three times greater than that which would be provided intravenously (i.e., 15 milligrams of Cyclosporin, 0.15 milligrams of RPM or 0.45 milligrams of FK 506 per kilogram of the patient's body weight).

If the patient is suffering from an autoimmune disease, the initial Cyclosporin, RPM or FK 506 dose should preferably consist of a dosage of 15 milligrams of Cyclosporin, 0.07 milligrams of RPM or 0.075 milligrams of FK 506 for each kilogram of the patient's body weight, and should be split in half and provided to the patient orally in two installments during the initial treatment day. An autoimmune disease patient can receive the initial dose intravenously as well, in which case, the dosage should be one third the total oral dosage (i.e., 5 milligrams of Cyclosporin, 0.025 milligrams of RPM or 0.025 milligrams of FK 506 for each kilogram of the patient's body weight).

Sometimes, a patient who will be treated by the method of the present invention has already received one of these immunosuppressants prior to beginning the treatment process prescribed by the present invention. In such a case, the last daily dosage administered to such a patient prior to the day he or she begins treatment as prescribed by the present invention is to be treated as the initial Cyclosporin, RPM or FK 506 dosage for purposes of this invention.

After being treated with the initial dose of Cyclosporin, RPM or FK 506, the patient is again examined by a physician. Typically, this second examination should occur on the day after the patient has received his or her initial dose of Cyclosporin, RPM or FK 506. However, in situations in which the patient has already received Cyclosporin, RPM or FK 506, this second examination can occur anywhere from one day after the patient's initial Cyclosporin, RPM or FK 506 dosage to one month after that date, depending primarily upon the patient's stability.

The second examination requires the physician to obtain information relating to patient examination criteria, step 3 of FIG. 1. These patient examination criteria used depends upon the medical condition for which the patient is receiving the immunosuppressant. When a patient is receiving Cyclosporin, RPM or FK 506 to prevent an adverse immune response relating to a transplanted heart or kidney, or an autoimmune disease, the patient examination criteria are toxicity, treatment efficacy and Cyclosporin, RPM or FK 506 whole blood levels. When a patient is receiving Cyclosporin, RPM or FK 506 to prevent an adverse immune response relating to a transplanted liver, there are three additional patient examination criteria: creatinine level, bilirubin level and SGOT and SGPT levels. In the preferred embodiment, information about a patient's alkaline phosphatase level and whether he or she is having mechanical problems will also be obtained during the second patient examination when that patient is receiving Cyclosporin, RPM or FK 506 to prevent an adverse immune response relating to a transplanted liver.

A physician determines whether a patient is experiencing toxicity, i.e., toxicity from the previously administered Cyclosporin, RPM or FK 506, by evaluating the patient's neural toxicity, diabetogenicity and nephrotoxicity. In the preferred embodiment, the factors analyzed to ascertain neural toxicity are tingling or loss of sensation, tremors and trouble sleeping. Diabetogenicity is determined from evaluating the patient's blood glucose level; and if the patient is suffering from hyperglycemia, then information about the treatment required to alleviate that problem will also be necessary for the diabetogenicity determination. Nephrotoxicity is determined by measuring the patient's creatinine level to see whether it has changed from the initial (or previous) examination, and if so, in what manner.

In the case of organ transplant patients, treatment efficacy pertains to whether the patient is rejecting the transplanted organ. The only truly accurate way to tell if a patient is rejecting a transplanted organ is to perform a biopsy and to do a histological evaluation of the tissue. Nevertheless, physicians skilled in the art can use well known surrogate markers to make estimates about rejection, e.g., liver enzymes can be used with respect to transplanted livers and the creatinine level can be used with respect to transplanted kidneys. However, surrogate markers cannot be used to determine rejection of a transplanted heart, in which case, a biopsy must be performed to make that determination.

Patients who are receiving Cyclosporin, RPM or FK 506 as a treatment for an autoimmune disease are examined for treatment efficacy as well. However, the examination is not geared towards rejection of a particular organ per se, but rather to determine whether the Cyclosporin, RPM or FK 506 is providing the desired effect. Autoimmune diseases have markers which physicians use to judge the improvement or deterioration of the condition. For example, in the case of psoriasis, the condition of the patient is measured using a standardized test called the PASI (psoriasis area severity index) score. This score indicates the severity of the patient's disease. Each autoimmune disease has its own marker(s), which are known to physicians skilled in the art. It is these markers which are used to determine if the Cyclosporin, RPM or FK 506 is producing the desired effect.

The current level of Cyclosporin, RPM or FK 506 contained in a patient's whole blood, i.e., the Cyclosporin, RPM or FK 506 whole blood level, is determined in the preferred embodiment through whole blood analysis by enzyme-linked immunoassay ("EIA") as described in the article written by W. J. Jusko et. al, entitled *Monitoring FK 506 concentrations in Plasma and Whole Blood*, published in December of 1991 on page 2732 of the *Transplantation Proceedings*.

The patient's creatinine level, bilirubin level, SGOT and SGPT levels, and alkaline phosphatase level can all be measured by any of the well established means which exist in the prior art, including biochemical blood test analysis. Physicians skilled in the art are capable of determining whether a patient is having mechanical problems by analyzing the patient's alkaline phosphatase level in conjunction with other well established factors.

Once the second examination is completed, a characterization is assigned to each of the patient examination criteria, step 4 of FIG. 1. The characterization chosen to describe each of the patient examination criteria comes from a predetermined standardized range of characterizations for each criterion.

The toxicity criterion can be characterized as "none", "mild", "moderate" or "severe". The characterization which should be chosen to describe the patient's toxicity level (or severity) is based upon an evaluation of the patient's neural toxicity, diabetogenicity and nephrotoxicity.

If a physician is not experienced in determining what characterization to use to describe the degree of toxicity being experienced by a patient, an expert system can be used, and it is in the preferred embodiment, to provide the appropriate characterization (or in some cases the two most appropriate characterizations when two are equally applicable), by evaluating characterizations assigned to a plurality of toxicity determination criteria (how this is done is discussed below). Like the patient examination criteria, each toxicity determination criterion is assigned a characterization from a predetermined standardized range of applicable characterizations. The information necessary for determining the appropriate characterization to describe each of the toxicity determination criteria should be obtained during the toxicity portion of the patient examination.

The first toxicity determination criterion is the tingling/loss of sensation toxicity determination criterion, a criterion which pertains to whether the patient is experiencing tingling or loss of sensation anywhere. The choice of characterizations for the toxicity/loss of sensation toxicity determination criterion are "none", "mild", "moderate" and "severe". The characterization "none" describes the situation in which the patient experiences no tingling or loss of sensation. The characterization "mild" describes the situation in which the patient experiences a slight tingling sensation in the ends of his or her fingers. If a patient experiences severe or moderate tingling without a complete loss of sensation (e.g., "pins and needles"), then the toxicity/loss of sensation toxicity determination criterion should be described as "moderate". However, if a patient experiences numbness or a complete loss of sensation, the toxicity/loss of sensation toxicity determination criterion should be described as "severe".

The second toxicity determination criterion is the tremor toxicity determination criterion, a criterion which pertains to whether the patient has been experiencing tremors. The following four characterizations can be used to describe that toxicity determination criterion: "none", "mild", "moderate" and "severe". The tremor toxicity determination criterion is described as "severe" if a patient experiences one or more seizures. The tremor toxicity determination criterion is described as "mild" if a patient experiences minor or mild twitching. If a patient experiences severe twitching without loss of consciousness, then the patient's tremor toxicity determination criterion should be described as "moderate". Finally, if a patient does not experience any twitching or seizures, then the characterization which should be used to describe the tremor toxicity determination criterion should be "none".

The next toxicity determination criterion is the trouble sleeping toxicity determination criteria, a criterion which pertains to whether the patient has been having trouble sleeping. Any of the following characterizations can be used to describe that toxicity determination criterion: "none", "mild", "moderate" and "severe". The characterization "none" is used to describe a patient who is able to get a restful, uninterrupted good night's sleep. The characterization "mild" is used to describe a patient who is sleeping through the night, but experiences nightmares (i.e., "technicolor dreams"), significant tossing and turning, and/or an fitful sleep. The "moderate" characterization is used to describe a patient who experiences interrupted sleep, i.e., he or she continuously wakes-up during his or her sleep period. The "severe" characterization is used to describe a patient who is completely unable to sleep and suffers from insomnia.

The next to last toxicity determination criteria is the diabetogenicity toxicity determination criterion. The characterizations which can be used to describe the diabetogenicity toxicity determination criterion are self explanatory and consist of "Hyperglycemia requiring insulin", "Hyperglycemia requiring oral agents", "slightly elevated blood sugars", and "normal glucose". Which characterization a physician will select for this toxicity determination criterion will depend completely upon what the physician observes during his or her toxicity examination of the patient. Specifically, the information he or she observes with respect to the patient's diabetogenicity.

The final toxicity determination criterion is the change in creatinine toxicity determination criterion, a criterion which pertains to how the patient's creatinine level has changed from the patient's last examination to the present one. Each of the following characterizations can be used to describe this toxicity determination criterion: "none", "slight rise", "steady rise", and "sharp increase". If the patient's creatinine level remains constant or decreases, then the proper characterization to describe this toxicity determination criteria is the "none" characterization. If the patient's creatinine level increases, but that increase is less than 0.3 milligrams per deciliter of blood plasma, the appropriate characterization to describe that increase is "slight rise". If the increase is between 0.3 and 0.5 milligrams per deciliter of blood plasma, then the appropriate description for the creatinine toxicity determination criterion is the "steady rise" characterization. Finally, if the increase in the creatinine level is greater than 0.5 milligrams per deciliter of blood plasma, the appropriate characterization to describe the increase is the "sharp increase" characterization.

Moving back to the patient examination criteria, the rejection criterion can be characterized as "none", "mild", "moderate" or "severe". The rejection criterion characterization can be made by analyzing the surrogate marker(s) appropriate for the transplant type. However, to insure accuracy, the preferred embodiment of the present invention requires that the characterization chosen be based upon an analysis of a biopsy.

The determination as to whether a patient's rejection is "none", "mild", "moderate" or "severe" in the preferred embodiment involves a three part analysis of the biopsy. First, the biopsy is examined to determine the degree of antibody cellular infiltration. Next, the biopsy is examined to determine the degree of parenchymal damage. Finally, the biopsy is examined to determine the degree of vascular lesions. Each of those evaluations is characterized by those skilled in pathology as either "none", "mild", "moderate" and "severe". In addition, each of those characterizations is utilized by pathologists to arrive at a final rejection characterization of the biopsy as "none", "mild", "moderate" and "severe". That being the case, in the preferred embodiment of the present invention, it is suggested that the characterization assigned to the rejection criterion be the same as the characterization assigned by a pathologist.

The desired effect criterion can be characterized as "none", "minimal", "moderate" and "good". The manner in which the desired effect criterion will be characterized will vary because each autoimmune disease has its own marker (s) which are evaluated in a different manner known to those skilled in the art. For example, in psoriasis, those skilled in the art will be able to characterize the severity of the disease, and in turn the desired effect by utilizing the PASI score.

The Cyclosporin, RPM or FK 506 whole blood level criterion can be characterized as "high", "low" and "OK".

The Cyclosporin whole blood level is considered "high" if the whole blood contains more than 500 nanograms of Cyclosporin per milliliter of blood. It is considered "low" if the whole blood contains less than 100 nanograms per milliliter of blood. If the patient's Cyclosporin whole blood level is between 200 and 350 nanograms per milliliter of blood, it is considered "OK".

The Rapamycin whole blood level is considered "high" if the whole blood contains more than 15 nanograms of Rapamycin per milliliter of blood. It is considered "low" if the whole blood contains less than 4 nanograms per milliliter of blood. If the patent's Rapamycin whole blood level is between 6 and 12 nanograms per milliliter of blood, it is considered "OK".

The FK 506 whole blood level is considered "high" if the whole blood contains more than 30.0 nanograms of FK 506 per milliliter of blood. It is considered "low" if the whole blood contains less than 10.0 nanograms per milliliter of blood. If the patient's Cyclosporin whole blood level is between 15 and 25 nanograms per milliliter of blood, it is considered "OK".

Although the range of characterizations which can be assigned to the Cyclosporin, RPM or FK 506 whole blood level criterion have been equated with numerical values, the equated numerical values are only median values. As mentioned before, the pharmacokinetics of Cyclosporin, RPM and FK 506 are such that there is a large inter-individual variability. What might be considered a "high" Cyclosporin, RPM or FK 506 whole blood level for one patient may be "low" for another patient. The characterization range used by the present invention to describe a patient's whole blood level are such that a physician has room to characterize the data concerning the patient's Cyclosporin, RPM or FK 506 whole blood level in a manner that properly describes the appropriate level with respect to the particular patient, regardless of the mean values assigned to the characterizations as described herein. This aspect applies equally with respect to the other criteria characterizations associated with median numerical values as well.

The creatinine level criterion can be characterized as "none", "mild", "moderate" and "severe". The creatinine level is considered "mild" if the patient's current level has increased by less than 0.3 milligrams per deciliter of blood versus the previously measured creatinine level. It is considered "moderate" when the patient's current level has increased between 0.3 and 0.5 milligrams per deciliter as compared to the patient's previously measured creatinine level. If the patient's creatinine level has increased by more than 0.5 milligrams per deciliter as compared with his or her previously measured creatinine level, then it is considered "severe". "None" is used to describe the situation where the patient's current creatinine level is less than or equal to his or her previous level.

The bilirubin level criterion can be characterized as "OK" and "high". A patient's bilirubin level is considered to be "OK" if it is less than or equal to 1.0 milligram per deciliter. On the other hand, if a patient has a bilirubin level above 1.0 milligram per deciliter, then the patient's bilirubin level is considered "high".

The only characterization choices applicable to the SGOT and SGPT levels criterion is whether they are increasing or decreasing (in the preferred embodiment, "yes" denotes increasing and "no" denotes decreasing). If either the SGOT or SGPT level is greater than 50 International Units per liter, then the SGOT and SGPT levels are increasing. If both are less than or equal to 50 International Units per liter, then the SGOT and SGPT levels are decreasing.

Once a physician is ready and able to assign characterizations to the patient examination criteria (including the toxicity determination criteria, if necessary), he or she is ready to deliver the assigned characterizations to the expert system of the present invention, step 5 of FIG. 1, so as to receive information concerning the course of action to be taken with respect to the patient's Cyclosporin, RPM or FK 506 treatment. In the preferred embodiment, that information will include an instruction concerning the patient's next Cyclosporin, RPM or FK 506 dosage.

The expert system of the present invention comprises a processor, an input means, an output means and a means for storing data (which is internal memory and/or external storage such as a hard disk drive or a 3½ inch floppy disk and associated drive). The preferred embodiment includes a personal computer ("PC") such as an IBM®, IBM®- compatible or a Macintosh® having at least 124K bytes of memory, a hard disk drive and a standard computer processor, such as an 80386. In the preferred embodiment, the PC has a keyboard, for receiving input data, and a color monitor, for receiving output data. A light pen, a mouse or a touch screen can be used in place of and/or in addition to the keyboard where appropriate, and a printer or an external output file can be substituted for the monitor.

In the preferred embodiment, the hard disk drive of the computer contains an expert computer program written in an AI language such as Prolog. In the preferred embodiment, the expert computer program pertains to one of the following four medical conditions: prevention of heart transplant rejection, prevention of liver transplant rejection, prevention of kidney transplant rejection or prevention of an autoimmune disease flare-up.

No matter which medical condition the expert computer program pertains to, the routines contained therein are the same. However, which medical condition the expert computer program pertains to affects the patient examination criteria (described above) utilized in the routines of the expert computer program. The source code for the computer programs written in Prolog (one for each of four medical conditions treated by each of the immunosuppressants— Cyclosporin, RPM and FK 506) are contained in the Microfiche Appendix.

It should be noted that the expert system of the present invention could be designed in a way in which each of the four expert computer programs are contained in the storage means and the physician user (i.e., the physician or his or her assistant) could select any one of those programs. The selected program would be loaded into the computer's internal memory and then executed.

The expert computer program includes a first routine which prompts a user, through the monitor, to enter the characterizations assigned to the patient examination criteria applicable to the medical condition being treated. The expert computer program has a second routine for selecting the Cyclosporin, RPM or FK 506 dosage instruction.

The second routine searches through a knowledge base (which can be integrated into the expert computer program or stored separately in either internal memory or external storage, provided the expert computer program has access to it), having rules which designate one of a plurality of Cyclosporin, RPM or FK 506 dosage instructions to every possible combination of characterizations which can be assigned to the applicable patient examination criteria, to find a rule which covers the characterizations assigned to the applicable patient examination criteria and entered into the expert system. The dosage instructions can include the following: "No change in dosage required", "You may consider a small increase in the dosage", "Increase dosage" and "Decrease dosage".

FIG. 9 provides a chart of rules which shows the patient examination criteria applicable to a heart or kidney transplant patient or an autoimmune disease affected patient, and which relates characterizations used to describe those criteria with FK 506 dosage instructions. It should be noted again that the efficacy criterion is the rejection criterion for the heart or kidney transplant patient and the desired effect criterion for the autoimmune disease patient. FIG. 10 provides a similar chart of rules which show the patient examination criteria applicable to a liver transplant patient, and which relates characterizations used to describe those criteria with FK 506 dosage instructions.

The charts contained in FIGS. 9 and 10 work as follows. Each column (i.e., a criterion selection column) after the first two columns on the left contains a rule with the designation on the top row being the dosage instruction. The "x" in each criterion selection column designates the characterization (s), in the second column, for a particular criterion, in the first column. When a criterion selection column does not designate a characterization for a particular criterion, the characterization assigned to that criterion does not affect the rule applying to that column. In addition, since only one characterization can be assigned to each criterion at a time, multiple designations in the same criterion selection column indicates either/or. Hence the rule in the first criterion selection column (i.e., the third column from the left) of FIG. 9 would be read as follows: when the toxicity criterion is either "none" or "mild" and the efficacy criterion (i.e., rejection criterion for transplant patients and desired effect criterion for autoimmune disease patients) is "none" and the FK 506 whole blood level criterion is "OK", then the FK 506 dosage instruction is "no change" irrespective of the prednisone dosage. (Prednisone is discussed below.)

Once the appropriate rule has been selected, the expert computer program obtains the dosage instruction from that rule. Subsequently, a third routine outputs the instruction to the monitor.

The expert computer program also contains in the preferred embodiment, additional routines (similar to the three just described) which are utilized in determining at least one toxicity criterion characterization. The first of these additional routines prompts a user, through the monitor, to enter the characterizations assigned to the toxicity determination criteria. The second of these additional routines searches through an additional knowledge base (i.e., a toxicity determination knowledge base), which the expert computer program has access to, to find a rule which covers the characterizations assigned to the toxicity determination criteria and entered into the expert system. The toxicity determination knowledge base contains rules which designate at least one toxicity criterion characterization to every possible combination of characterizations which can be assigned to the toxicity determination. (In some cases there are two.) FIG. 11 provides a chart of rules relating characterizations applicable to the toxicity determination criteria to toxicity criterion characterizations. (This chart operates in essentially the same way as the charts in FIGS. 9 and 10). Once a rule has been selected, the expert computer program through the third additional routine outputs the characterization(s) which should be assigned to the toxicity criterion to the color monitor for the physician user's use.

In addition to providing the Cyclosporin, RPM or FK 506 dosage instruction, the expert system of the present invention is also capable of providing, in the preferred embodiment, at least one additional instruction concerning the course of action a physician should take with respect to the treatment of a patient with one or more additional immunosuppressant agents which he or she may administer along with the Cyclosporin, RPM or FK 506 to the patient.

If an additional immunosuppressant agent is to be administered to the patient along with Cyclosporin, RPM or FK 506, the preferred immunosuppressant agent is prednisone; and an initial dose of prednisone should be administered along with the Cyclosporin, RPM or FK 506, step 200 of FIG. 1, after step 2 of FIG. 1 and before step 3 of FIG. 1.

The means by which the expert system determines and provides an instruction concerning the course of action which should be taken with respect to the prednisone treatment ("prednisone treatment instruction") is essentially the same as the means by which the expert system selects the Cyclosporin, RPM or FK 506 dosage instruction and the toxicity criterion characterization(s). The expert computer program in the preferred embodiment contains in its routine for eliciting and receiving the patient examination criteria applicable to the medical condition being treated, a subroutine for eliciting and receiving a characterization describing the current prednisone dosage administered to the patient ("a prednisone dosage criterion").

The characterizations which are used to describe the patient's current prednisone dosage are "high", "low" and "not on". "High" is the designation used to describe prednisone dosages which are greater than 10 milligrams. "Low" is the designation used to describe prednisone dosages which are less than or equal to 10 milligrams. The characterization "not on" is used when the patient is not receiving prednisone.

After receiving the characterization assigned to the prednisone dosage criterion, the expert computer program can, through another routine, select the prednisone treatment instruction by searching through a prednisone treatment knowledge base, which contains rules which designate one of several prednisone treatment instructions to every possible combination of characterizations which can be assigned to the prednisone dosage criterion and the efficacy criterion (either the rejection criterion for transplant patients or the desired effect criterion for autoimmune patients) to find a rule which covers the characterizations assigned to those two criteria. FIG. 12 provides a chart of rules showing which characterizations used to describe the prednisone dosage criterion and efficacy criterion will provide which prednisone treatment instruction. (This chart operates in essentially the same way as the charts of FIGS. 9 and 10.) Once the appropriate rule is found, the prednisone treatment instruction is output to the monitor via another expert computer program routine.

When prednisone is being administered along with Cyclosporin, RPM or FK 506, it may have an effect upon the course of action a physician should take with respect to the patient's treatment. This fact is taken into account by one of the rules contained in the knowledge base used by the expert system of the present invention to determine the Cyclosporin, RPM or FK 506 dosage instruction. Hence, when the expert system determines the appropriate Cyclosporin, RPM or FK 506 dosage instruction, and the patient is receiving prednisone along with Cyclosporin, RPM or FK 506, the dosage instruction provided by the expert system takes the prednisone treatment into account.

In addition to the dosage instruction and the prednisone treatment instruction, the expert system of the present invention is also capable of providing, in the preferred embodiment comments concerning potential problems and/or means for solving those problems which cannot be corrected by Cyclosporin, RPM or FK 506, alone or in conjunction with additional immunosuppressant agents. These comments include the following: "Should consider alternative therapy (Immuran or OKT3)", "Check for Hepatic Artery Thrombosis, Hepatitis or Rejection" or "Surgery may be required to correct the problem."

If the toxicity criterion is characterized as severe and the efficacy is characterized as severe, then, and only then, the first comment listed above will be provided. If the SGOT or SGPT levels are increasing, then the expert system will output the third comment listed above. (A discussion of when the second comment listed above is output is described immediately below.) The expert system of the preferred embodiment contains one or more routines for determining and providing these comments.

In a preferred version of the liver transplant expert computer program, the physician user is asked whether the patient's alkaline phosphatase level is increasing. The answer to the alkaline phosphatase question depends on the following alkaline phosphatase rules: If the alkaline phosphatase level of the patient is above 150 International Units per liter, then it is considered increasing; if it is less than or equal to 150 International Units per liter, then it is decreasing. (In the preferred embodiment "yes" denotes increasing and "no" denotes decreasing).

In order to answer the alkaline phosphatase question, the patient's alkaline phosphatase level must be measured. In the preferred embodiment, that measurement is made during the second examination.

If the alkaline phosphatase level is increasing according to the alkaline phosphate rules, the expert computer program will query the physician user as to whether there are any mechanical problems. The physician user should reply "no" if the physician does not suspect that there are any mechanical problems, and this will trigger the expert system to treat the alkaline phosphatase level as though it were characterized as decreasing, which in turn, has no effect on the patient's Cyclosporin, RPM or FK 506 treatment and no instructions or comments are received. If on the other hand, the physician believes that there is a mechanical problem (e.g., an obstruction of the portal vein), then the physician user should respond "yes". That response will cause the expert system to output the second comment listed above.

Once a characterization for each patient examination criterion is delivered to the expert system and the expert system has selected the appropriate instruction(s) (and comments) in the manner described above, those instruction(s) will then be output to the color monitor (with any applicable comment(s)), so that the physician user can receive it (or them) from the expert system, step 6 of FIG. 1.

The final step involved in this embodiment is to administer a next dose of the immunosuppressant Cyclosporin, RPM or FK 506 to the patient in accordance with the expert system generated dosage instruction, step 7 of FIG. 1.

Three other embodiments of the present invention involve determining the exact numerical dosage of Cyclosporin, RPM or FK 506 to be administered to a patient at a given time during the treatment process. The first of these three embodiments is referred to as the "Non-Expert System Embodiment", the second is referred to as the "Expert System Embodiment For Decreasing Dosages", and the third is referred to as the "Expert System Embodiment For All Dosages". The Expert System Embodiment For Decreasing Cyclosporin, RPM or FK 506 Dosages can only be used to determine the next dosage when the next dosage is being decreased with respect to the current Cyclosporin, RPM or FK 506 dosage, respectively.

Figure 3:
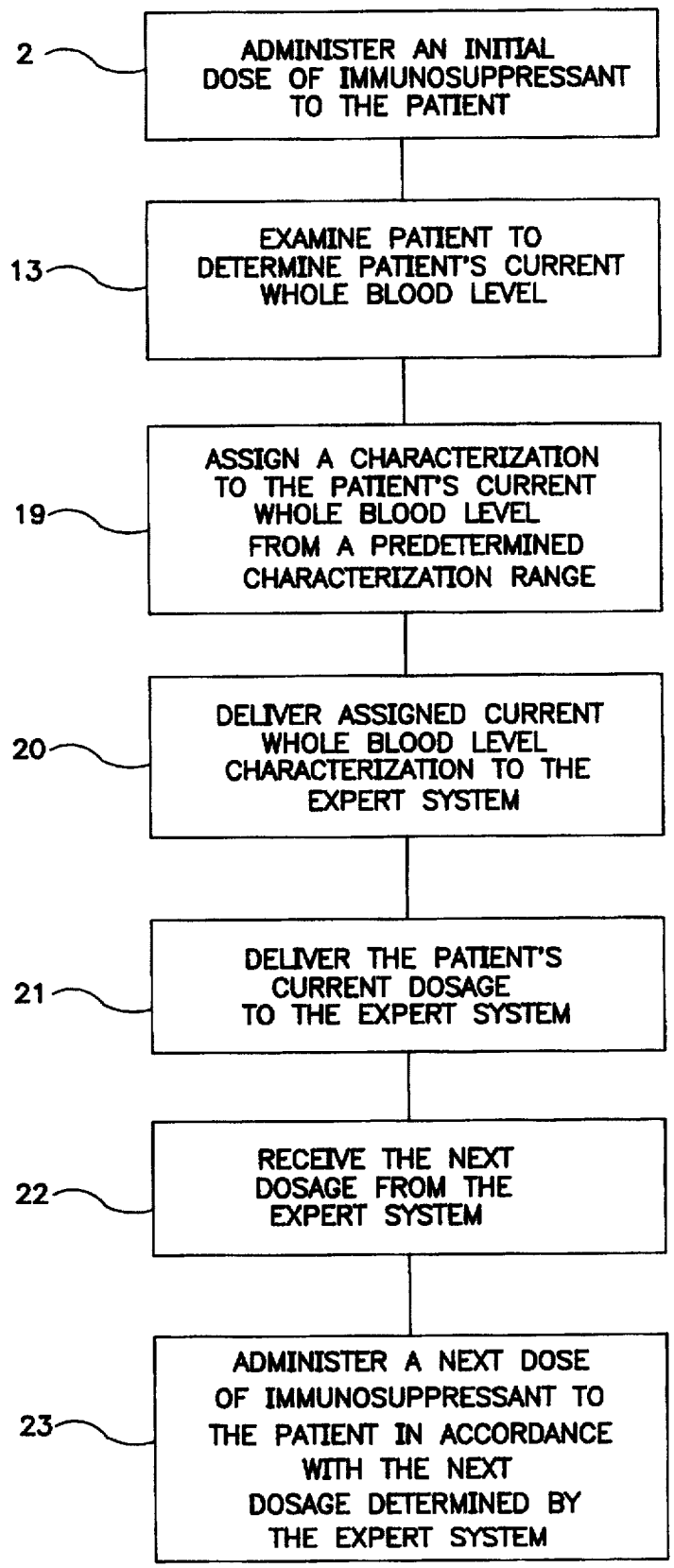
FIG. 3 is a flow chart depicting a third embodiment of the present invention.
Figure 4:
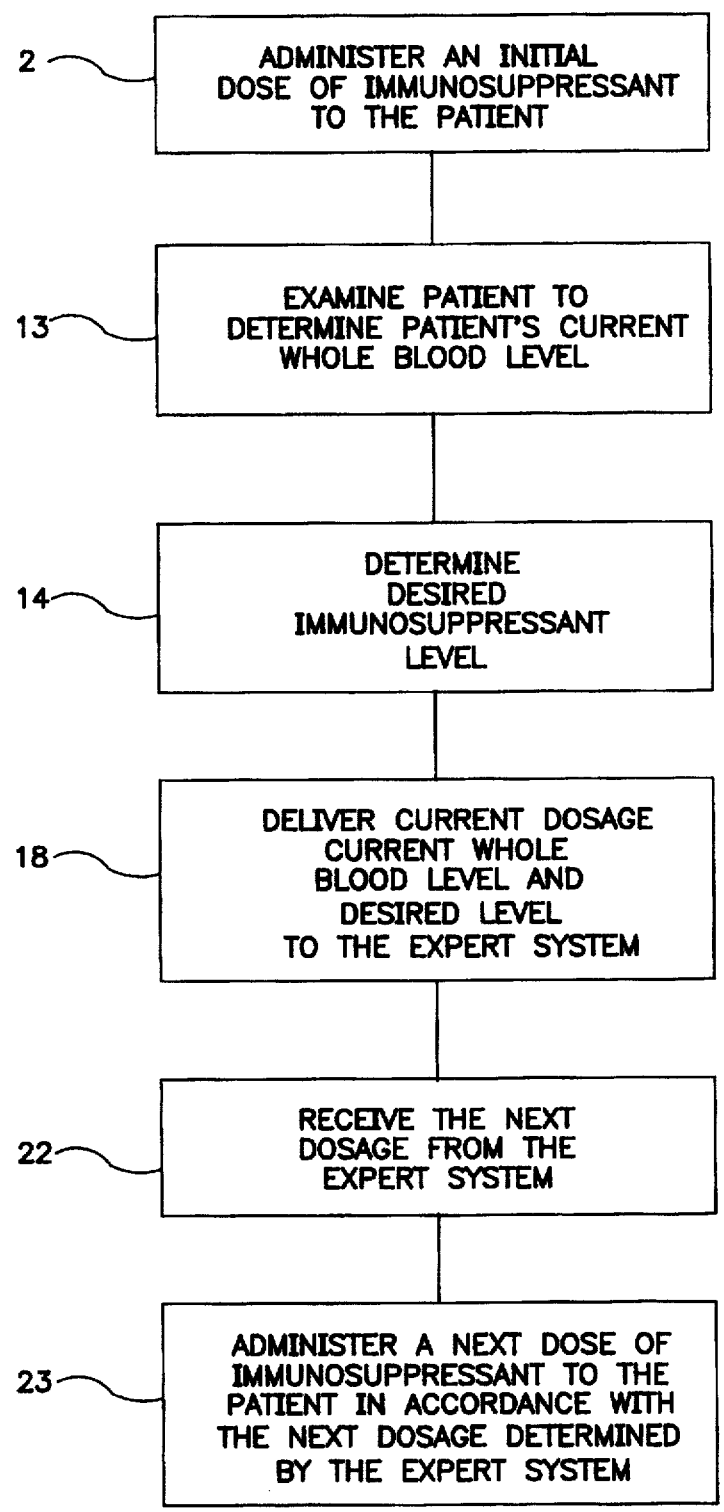
FIG. 4 is a flow chart depicting a fourth embodiment of the present invention.

All three of these embodiments begin with the administration of an initial dose of the immunosuppressant, i.e. Cyclosporin, RPM or FK 506, step 2 of FIGS. 2, 3 and 4, respectively. This step is exactly the same as step 2 of FIG. 1. The next step in all three of these embodiments is to examine the patient to determine his or her current Cyclosporin, RPM or FK 506 whole blood level, step 13 of FIGS. 2, 3 and 4, respectively. After that step, these additional embodiments take different courses to determine the patient's next dosage.

Referring to FIG. 2, the third step of the Non-Expert System Embodiment is for the physician to make a determination as to what he or she believes the desired Cyclosporin, RPM or FK 506 level for the patient should be, step 14 of FIG. 2. Generally, with respect to organ transplant patients, the rule is that the patient's Cyclosporin whole blood level should be increased or decreased by 50 nanograms per milliliter of whole blood, the patient's RPM whole blood level should be increased or decreased by 5 nanograms per milliliter or the patient's FK 506 whole blood level should be increased or decreased by 5 nanograms per milliliter of blood when the patient requires a higher or lower dosage of Cyclosporin, RPM or FK 506, respectively.

With respect to an autoimmune disease patient, the general rule is to increase or decrease the patient's Cyclosporin whole blood level by 25 nanograms per milliliter of whole blood, the patient's RPM whole blood level by 3 nanograms per milliliter of whole blood, and the FK 506 whole blood level by 3 nanograms per milliliter of whole blood when the patient requires a higher or lower dosage of Cyclosporin and FK 506, respectively. Since the physician knows the patient's current Cyclosporin, RPM or FK 506 whole blood level from the patient examination, he or she can use these rules to determine the desired Cyclosporin, RPM or FK 506 level for the patient.

It should be noted that any time portions of this process are repeated in any continuous manner (repetition of steps of this and other embodiments is discussed below) the desired Cyclosporin, RPM or FK 506 level determination will be affected by what the physician learns over time with respect to the patient. For example, if a transplant patient's initial Cyclosporin whole blood level was 300 nanograms per milliliter of whole blood, the initial RPM whole blood level was 20 nanograms per milliliter or the FK 506 whole blood level was 30 nanogram per milliliter of whole blood and a physician wishes to increase that level, the physician would increase that level to 350 nanograms of Cyclosporin, 25 nanograms of RPM or 35 nanograms of FK 506 per milliliter of whole blood. However, if this dosage were to cause toxicity, then at no time should the patient's desired Cyclosporin level be greater than 350 nanograms, the patient's desired RPM level be greater than 25 nanograms or the patient's FK 506 level be greater than or equal to 35 nanograms per milliliter of whole blood.

Once the desired Cyclosporin, RPM or FK 506 level for the patient has been determined, the patient's current Cyclosporin, RPM or FK 506 dosage, the patient's current Cyclosporin, RPM or FK 506 whole blood level, and the desired Cyclosporin, RPM or FK 506 level for the patient are employed with the following relationships to determine the next Cyclosporin, RPM or FK 506 dosage, respectively at step 16 of FIG. 2:

For Cyclosporin (CyA):

$$ND = CD - ((((CL-DL)/CL)/(2.5+(CD/1500)\times 2.5))/CD) + ((0.2\times CD)\times (((1+d)-(1+e))/abs(((1+d)))))$$

wherein,

ND = the next CyA dosage,

CD=the patient's current CyA dosage,
CL=the patient's current CyA whole blood level,
DL=the desired CyA whole blood level for the patient,
RD=the patient's previous CyA whole blood level,
e=Cl–RD,
d=DL–RD.

For FK 506:

$$ND = CD - (((((CL-DL)/CL)/(1+(CD/40)))/CD) + ((0.2 \times CD) \times (((1+d)-(1+e))/abs((1+d)))))$$

wherein

ND=the next FK 506 dosage,
CD=the patient's current FK 506 dosage,
CL=the patient's current FK 506 whole blood level,
DL=the desired FK 506 whole blood level for the patient,
RD=the patient's previous FK 506 whole blood level,
e=CL–RD,
d=DL–RD.

For RPM:

$$ND = CD - (((((CL - DL)/CL)/(1 + (CD/30)))/CD) + ((0.2 \times CD) \times (((1 + d) - (1 + e))/abs((1 + d)))))$$

wherein,

ND=the next RPM dosage,
CD=the patient's current RPM dosage,
CL=the patient's current RPM whole blood level,
DL=the desired RPM whole blood level for the patient,
RD=the patient's previous RPM whole blood level,
e=CL–RD
d=DL–RD.

Determination of the next Cyclosporin, RPM or FK 506 dosage through use of the above relationships can be performed by employing several prior art devices and methods, including a calculator or conventional computer program. Moreover, a slight modification of the expert computer programs provided in the Microfiche Appendix is capable of performing this step, when the physician user selects the appropriate option (in those programs that option is the "Dosage Determination" option).

The final step of the Non-Expert System Embodiment is to administer a next Cyclosporin, RPM or FK 506 dose to the patient in accordance with the next Cyclosporin, RPM or FK 506 dosage determined through the above relationship, step 17 of FIG. 2.

Referring to FIG. 3, the third step of the Expert System Embodiment For Decreasing Dosages (i.e., the embodiment which can be used only when the next Cyclosporin, RPM or FK 506 dosage is being decreased with respect to the current Cyclosporin, RPM or FK 506 dosage) is to assign a characterization to the patient's current Cyclosporin, RPM or FK 506 whole blood level, step 19 of FIG. 3. The discussion provided above with respect to the characterizations which can be assigned to the Cyclosporin FK 506 whole blood level criterion in step 4 of FIG. 1 apply to this step as well. Once the appropriate characterization has been assigned to the patient's current Cyclosporin, RPM or FK 506 whole blood level, then that characterization is delivered to the expert system of the present invention, step 20 of FIG. 3, along with the patient's current dosage, step 21 of FIG. 3.

The expert system utilized by this embodiment contains the same elements as the expert system described with respect to the embodiment depicted by FIG. 1. The only differences are in the expert computer program and the knowledge base to which it has access. The expert computer program of this embodiment contains three routines. The first routine prompts the physician user, through the color monitor, to enter the characterization assigned to the patient's current Cyclosporin, RPM or FK 506 whole blood level and the patient's current dosage. The second routine, which has access to a knowledge base which contains rules which designate a next Cyclosporin, RPM or FK 506 dosage (which is less than the current Cyclosporin, RPM or FK 506 dosage) to every possible combination of the characterizations which can be assigned to the patient's current Cyclosporin, RPM or FK 506 whole blood level and values for the patient's current dosage, searches that knowledge base to find a rule which covers the characterization assigned to the patient's current Cyclosporin, RPM or FK 506 whole blood level and the patient's current dosage. The third routine outputs the next dosage to the color monitor so that the physician user can receive the next dosage from the expert system, step 22 of FIG. 3.

The final step of the Expert System Embodiment For Decreasing Dosages is to administer a next dose of to the patient in accordance with the dosage determined by the expert system, step 23 of FIG. 3.

Referring to FIG. 4, the third step of the Expert System Embodiment For All Dosages is for the physician to make a determination as to what he or she believes the desired Cyclosporin, RPM or FK 506 whole blood level of the patient should be, step 14 of FIG. 4. This step is the same step as step 14 of FIG. 2.

Next, the patient's current dosage, the patient's current whole blood level and the desired Cyclosporin, RPM or FK 506 level for the patient are delivered to the expert system of the present invention, step 18 of FIG. 4. The expert system utilized by this embodiment contains the same elements as the expert systems described with respect to the embodiment depicted by FIGS. 1 and 2. The only differences are in the expert computer program and the knowledge base to which it has access. The expert computer program of this embodiment contains three routines. The first routine prompts the physician user, through the monitor, to enter the patient's current dosage, the patient's current Cyclosporin, RPM or FK 506 whole blood level and the desired level for the patient. The second routine, which has access to a knowledge base which contains rules which designate a next dosage to every possible combination of values for the current dosage, Cyclosporin, RPM or FK 506 whole blood level and desired level, searches that knowledge base to find a rule which covers the characterization assigned to the patient's current whole blood level, the patient's current dosage and the desired level for the patient. The third routine outputs the next dosage to the monitor so that the physician user can receive the next dosage from the expert system, step 22 of FIG. 4.

The final step of the Expert System Embodiment For All Dosages is to administer a next dose of Cyclosporin, RPM or FK 506 to the patient in accordance with the dosage determined by the expert system, step 23 of FIG. 4.

Each of the embodiments described up to this point is a single pass embodiment (i.e., a one shot application) of the present invention which provides a physician user with either an instruction or an actual numerical dosage pertaining to the patient's next dosage. It is quite possible that a physician, who is continuously prescribing daily doses of Cyclosporin, RPM or FK 506, may employ any one of those embodiments to aid in getting on track in treating his or her patient, since a one shot application of this invention is extremely accurate in determining the appropriate course of action and/or next dosage.

However, once a patient begins treatment with one of the immunosuppressants, that patient must receive the medication for the remainder of his or her life, or else, he or she is susceptible to a rejection of a transplanted organ or a flare-up of an autoimmune disease. The Cyclosporin, RPM or FK 506 (and prednisone, if being administered) dosage a patient requires at a given time will change with the patient's stability. Thus, in order to be sure that a patient will continuously receive the proper dosage he or she requires throughout the remainder of his or her life, it is preferred that several of the embodiments described above, specifically the ones depicted in FIGS. 1, 2 and 4, include additional steps which make sure that the patient will continuously receive Cyclosporin, RPM or FK 506 (and prednisone, if it is being administered), and that a reassessment of the dosage is made in a systematic manner based on the patient's stability.

Such steps, will make sure, for example, that if a physician initially prescribes 15 milligrams of Cyclosporin, 0.07 milligrams of RPM or 0.075 milligrams of FK 506 for each kilogram of the patient's body weight and then employs any one of the embodiments described above to arrive at the next dosage, the physician will continue to administer Cyclosporin, RPM or FK 506 to the patient for the remainder of that patient's life, either with that next dosage or a new dosage determined by any of the embodiments described above, if one of those embodiments determines that a new dosage is required. Only through systematic reassessment can one be sure that a patient will be receiving the proper dosage throughout that patient's life. The addition of two steps to the embodiments of FIGS. 1, 2 and 4 can provide this. It should be noted that FIGS. 5, 6 and 7 are the same embodiments depicted in FIGS. 1, 2 and 4, respectively, with the addition of those two steps.

Figure 5:
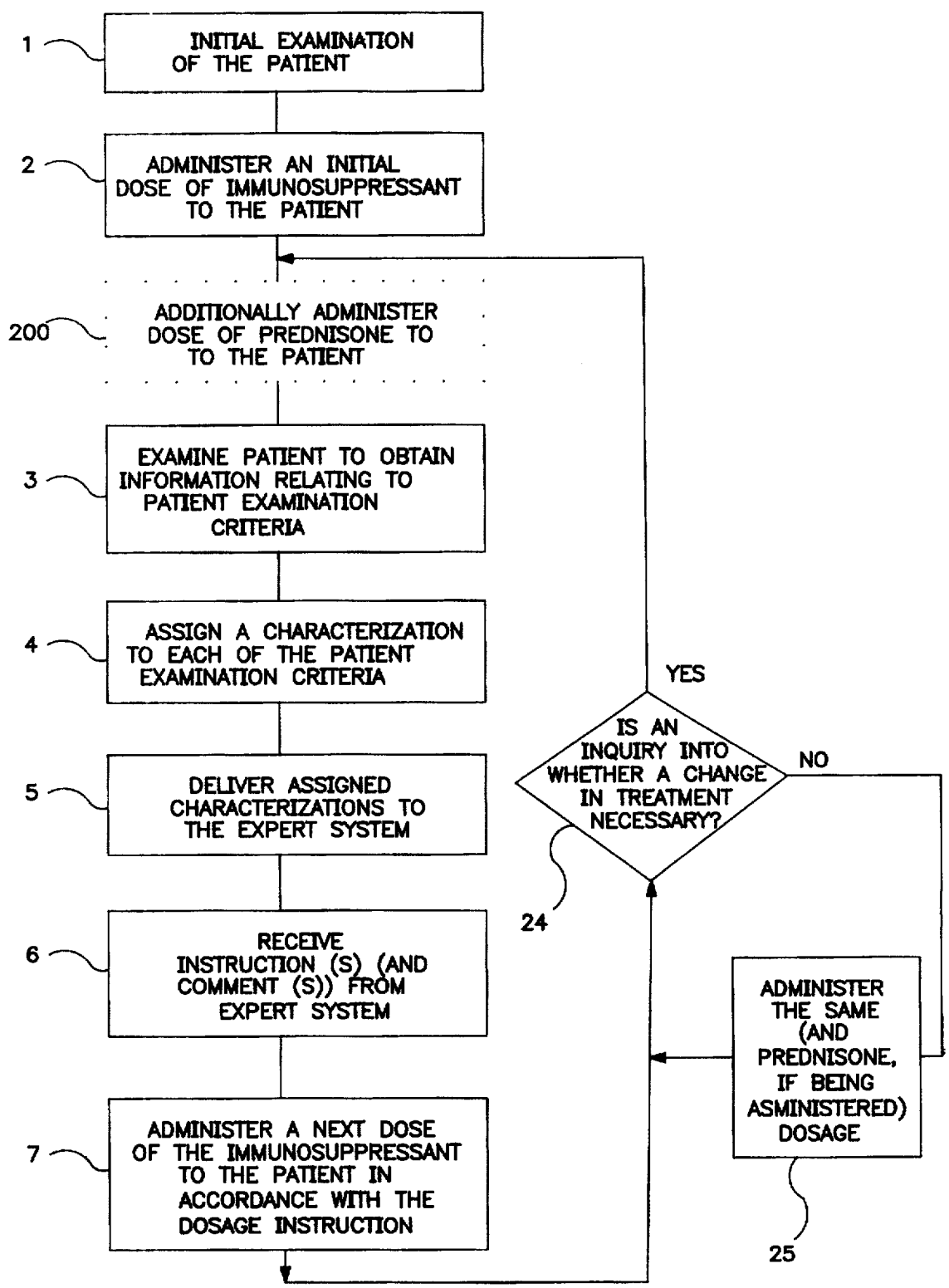
FIG. 5 is a flow chart depicting a variation of the first embodiment of the present invention with the addition of continuous loop steps.
Figure 6:
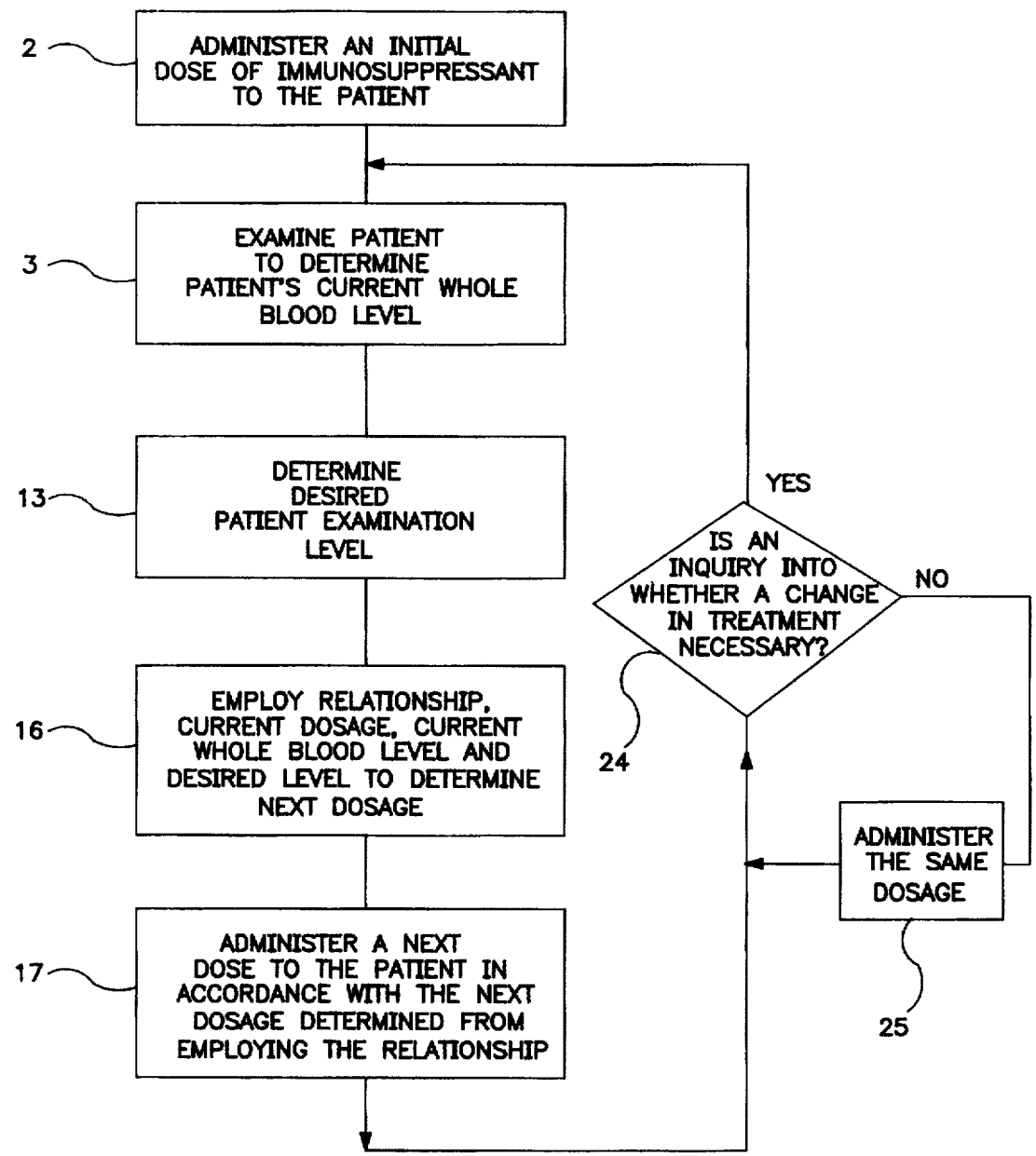
FIG. 6 is a flow chart depicting a variation of the second embodiment of the present invention with the addition of continuous loop steps.
Figure 7:
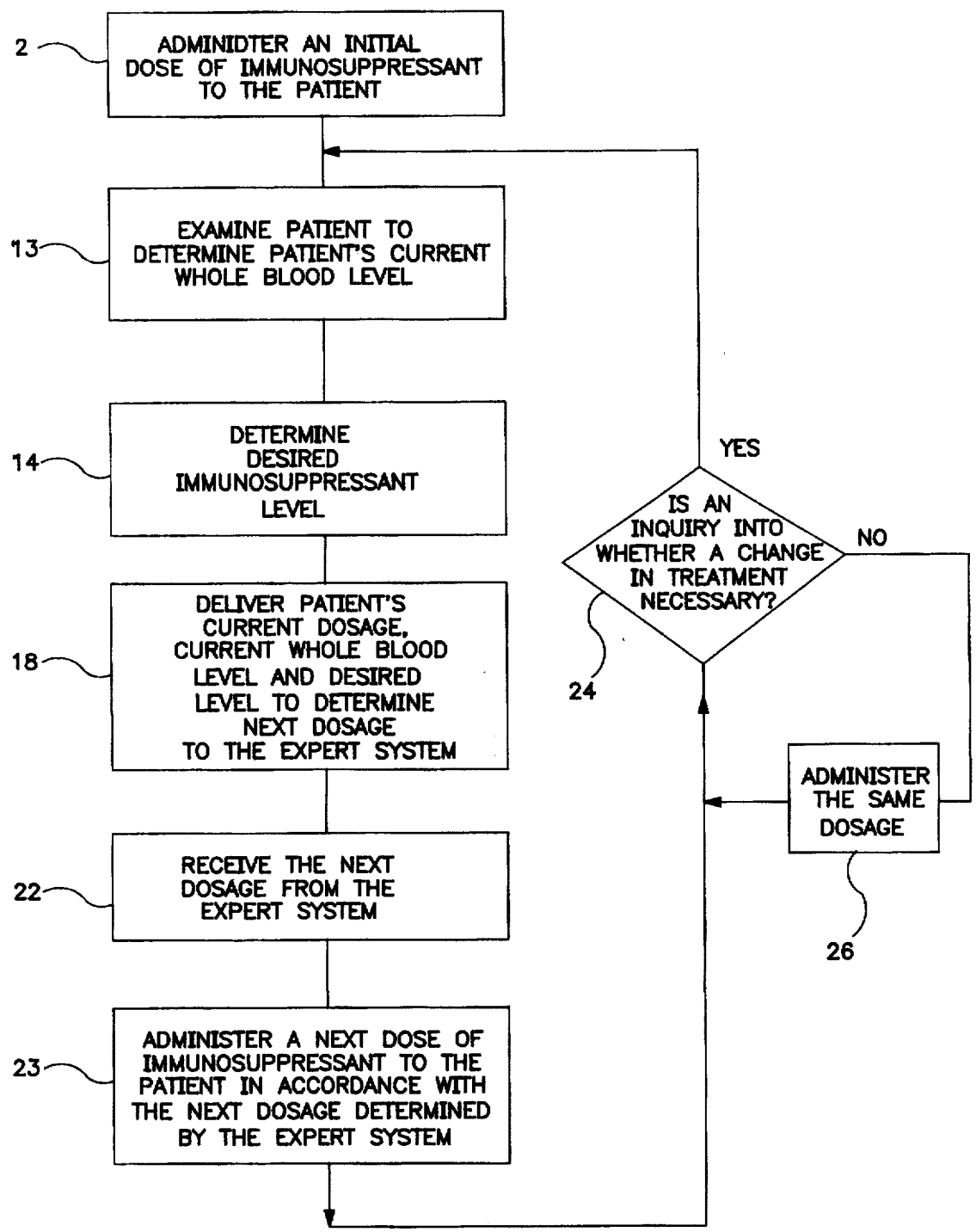
FIG. 7 is a flow chart depicting a variation of the fourth embodiment of the present invention with the addition of continuous loop steps.

One of those additional steps is the question whether an inquiry should be made as to whether a change in treatment is necessary (step 24 of FIGS. 5, 6 and 7). If the answer to that question is "no" in the embodiment of FIG. 5, the patient receives the same dosage (and prednisone, if being administered), step 25 of FIG. 5, as the patient previously received; thereafter, step 24 of FIG. 5 is repeated. Likewise, if the answer to the question of step 24 of the embodiment of FIG. 6 or 7 is "no", the patient receives the same dosage, step 25 of FIGS. 6 and 7, respectively, as the patient received previously; thereafter, step 24 of FIGS. 5 and 6 are repeated, respectively.

If the answer to the question contained in step 24 of FIG. 5, 6 or 7 is "yes", then a portion of the process of those embodiments are again repeated in a continuous loop, i.e., steps 3 through 24, steps 13 through 24 and steps 13 through 24, respectively.

In the preferred embodiment, the patient receives a dosage of Cyclosporin, RPM or FK 506 every day after he or she begins treatment under any of these embodiments for the remainder of his or her life. Therefore, step 24 should be encountered every day in each of those embodiments.

In the preferred embodiment, the response to step 24 should be "yes" in the following situations as well as in situations in which the patient is not considered stable: (a) for a transplant patient, every day for the first two weeks after the patient begins the process of the present invention. Thereafter, twice a week for the next two weeks; then weekly for the next two months; and then monthly for the rest of the patient's life; (b) for an autoimmune disease patient, twice a week for the first two weeks after the process of the present invention begins. Thereafter, weekly for the next month, and then, monthly for the rest of the patient's life.

Steps 24 and 25 of FIG. 5 and steps 24 and 26 of FIGS. 6 and 7 assure that a patient receives a dosage of Cyclosporin, RPM or FK 506 every day and that the dosage (and prednisone, if being administered) is reassessed in a systematic manner throughout the remainder of the patient's life.

Figure 8:
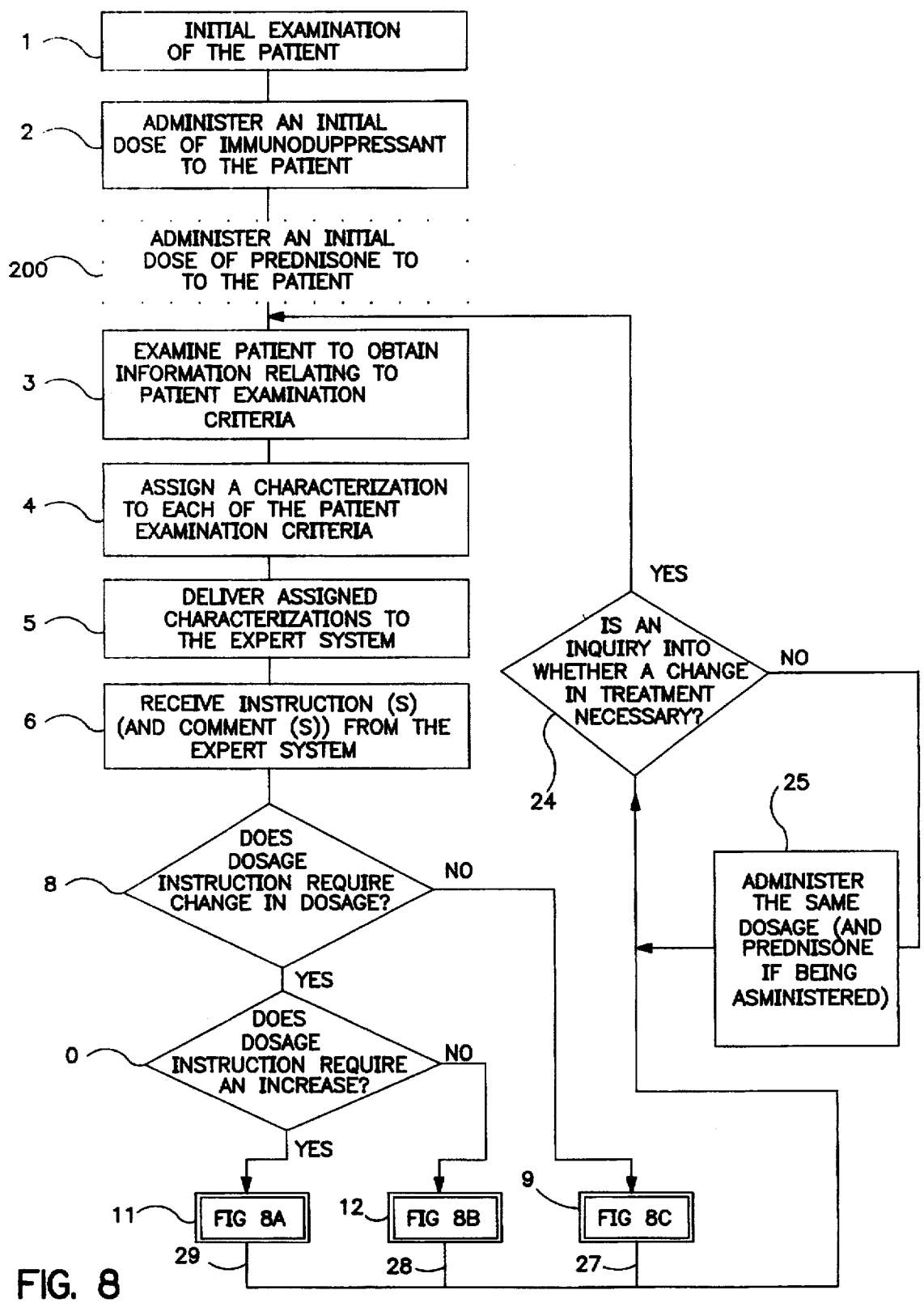
FIGS. 8, 8A, 8B and 8C are flow charts depicting a fifth embodiment of the present invention.

A preferred process of the present invention involves combining aspects of the embodiments depicted in FIGS. 1, 2 and 3 as described above. This combined embodiment begins with the same initial seven steps as the embodiment depicted in FIG. 1 (i.e., steps 1, 2, 200, 3, 4, 5, and 6 of FIG. 1), which are shown as steps 1, 2, 200, 3, 4, 5 and 6 of FIG. 8. Once those seven steps have been completed, the physician user will have received, as a minimum, a dosage instruction. Thereafter, step 8 of FIG. 8 is encountered. Step 8 of FIG. 8 requires a "yes" or "no" response to whether the dosage instruction requires a change.

Figure 8A:
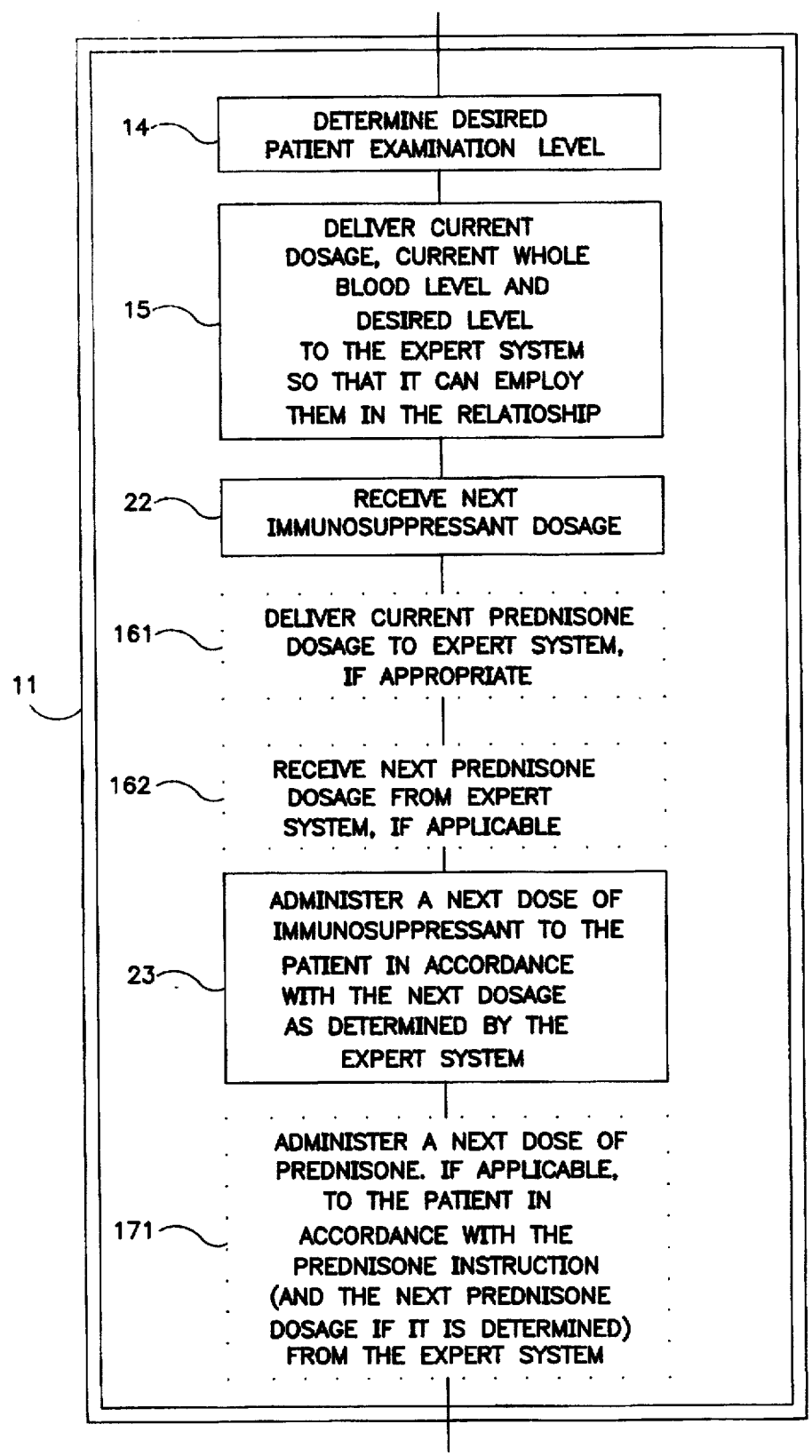
Figure 8B:
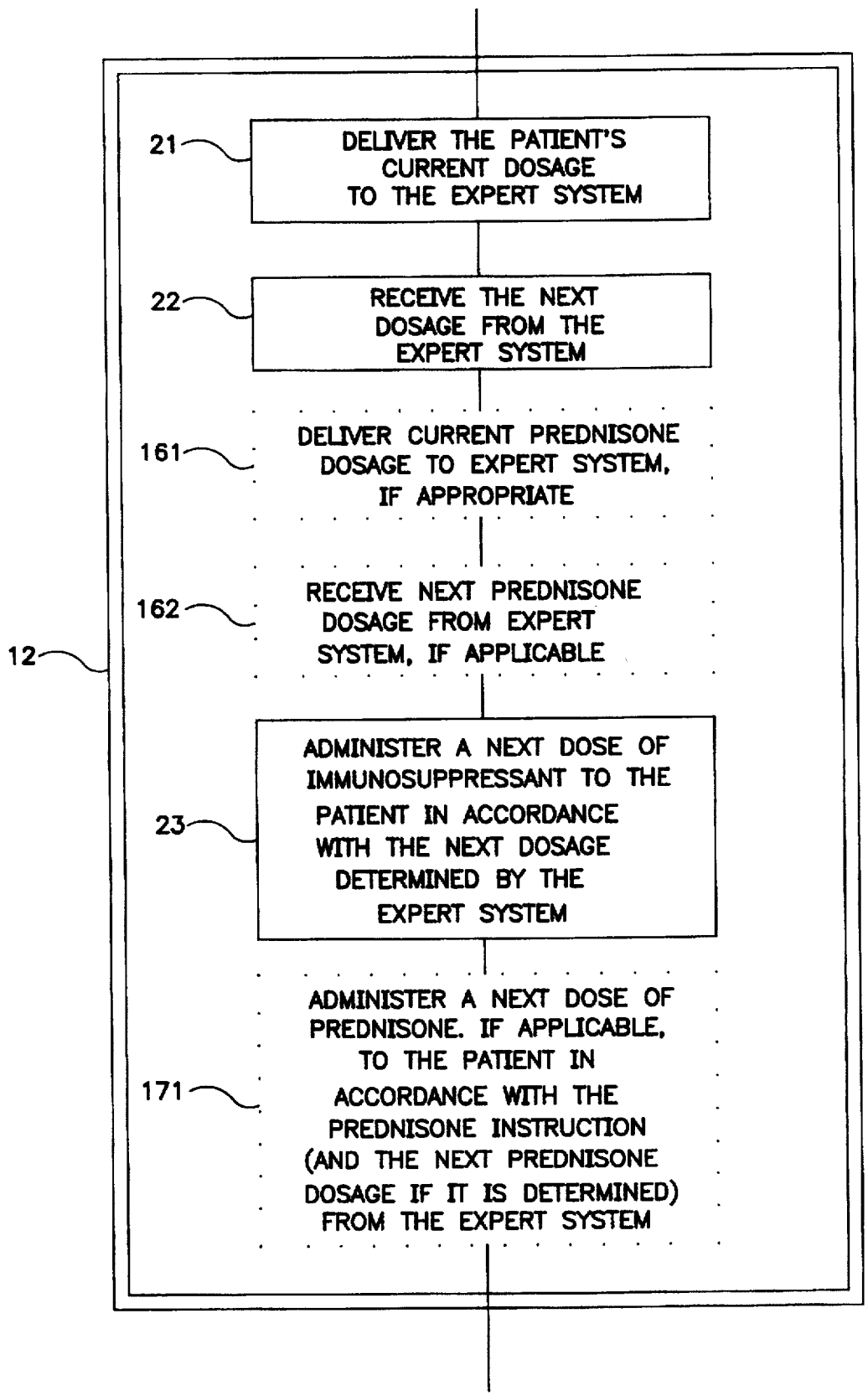
Figure 8C:
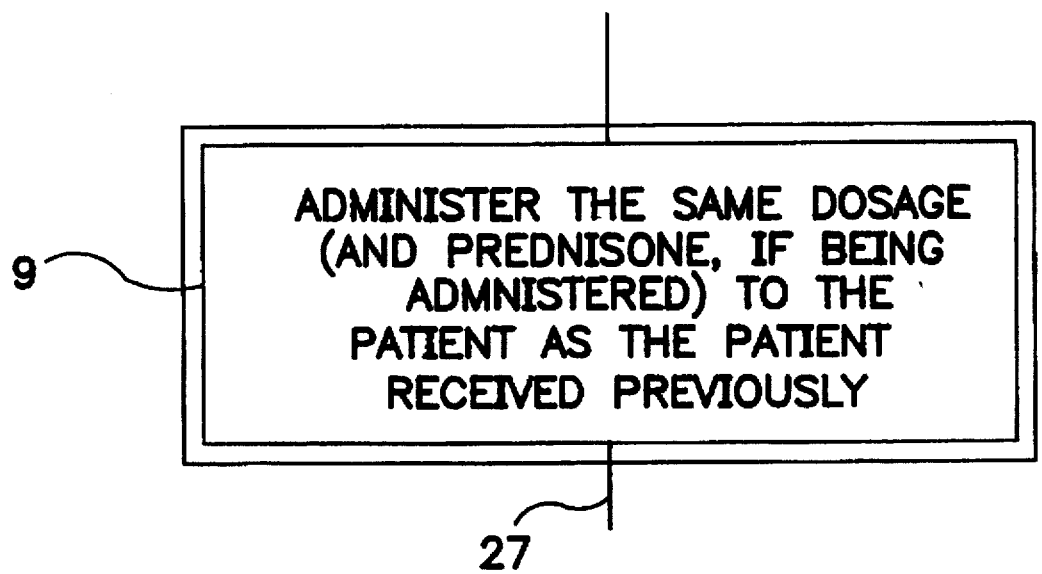

If the answer to the question of step 8 of FIG. 8 is "no", then the process of the combined embodiment continues with step 9 which is contained in FIG. 8C. Step 9 of FIG. 8C requires that the physician administer the same Cyclosporin, RPM or FK 506 (and prednisone, if being administered) dosage to the patient as the patient previously received.

If, however, the answer to the question of step 8 of FIG. 8 is "yes", then the process of the combined embodiment continues with step 10 of FIG. 8. Step 10 of FIG. 8 queries the physician user as to whether the dosage instruction requires an increase. If it does, then the process steps depicted in FIG. 8A are the next steps to be followed in this embodiment, step 11 of FIG. 8. Those process steps begin with determining the desired immunosuppressant level for the patient, step 14 of FIG. 8A; delivering the patient's current dosage, the patient's current Cyclosporin, RPM or FK 506 whole blood level and the desired Cyclosporin, RPM or FK 506 level for the patient to the expert system, step 15 of FIG. 8A; and then receiving the next FK 506 dosage from the expert system, step 22 of FIG. 8A. When the process of the combined embodiment entails following the steps depicted in FIG. 8A, the expert system determines the next Cyclosporin, RPM or FK 506 dosage by employing the following relationship:

For Cyclosporin (CyA):

$$ND=CD-((((CL-DL)/CL)/(2.5+(CD/1500)\times 2.5))/CD)+((0.2\times CD)\times (((1+d)-(1+e))/abs((1+d))))$$

wherein

ND=the next CyA dosage,

CD=the patient's current CyA dosage,

CL=the patient's current CyA whole blood level,

DL=the desired CyA whole blood level for the patient,

RD=the patient's previous CyA whole blood level, e=CL−RD, d=DL−RD.

For FK 506 :

$$ND=CD-((((CL-DL)/CL)/(1+(CD/40)))/CD)+((0.2\times CD)\times (((1+d)-(1+e))/abs((1+d))))$$

wherein

ND=the next FK 506 dosage,

CD=the patient's current FK 506 dosage,

CL=the patient's current FK 506 whole blood level,

DL=the desired FK 506 whole blood level for the patient,

RD=the patient's previous FK 506 whole blood level, e=CL−RD, d=DL−RD.

For RPM:

$$ND=CD-((((CL-DL)/CL)/(1+(CD/30)))/CD)+((0.2\times CD)\times(((1+d)-(1+e))/abs((1+d))))$$

wherein

ND=the next RPM dosage,

CD=the patient's current RPM dosage,

CL=the patient's current RPM whole blood level,

DL=the desired RPM whole blood level for the patient,

RD=the patient's previous RPM whole blood level, e=CL−RD d=DL−RD.

The expert system employed by the combined embodiment contains routines within its expert computer program necessary for carrying out steps 14, 15 and 22 of FIG. 8A.

The expert system of the combined embodiment of the present invention is capable of providing the numerical next prednisone dosage which a patient should receive when the patient is receiving prednisone along with Cyclosporin, RPM or FK 506 and the prednisone treatment instruction requires the prednisone dosage to be decreased. In accordance with this, the next two steps of the process depicted in FIG. 8A requires that the physician user deliver the current prednisone dosage to the expert system, step 161 of FIG. 8A, if appropriate, and then receive the next prednisone dosage step 162 of FIG. 8A, if applicable. The expert system of this embodiment of the present invention contains a routine for eliciting and receiving that dosage, a routine for determining the next prednisone dosage and a routine which outputs that dosage to the color monitor.

The expert system of the combined embodiment determines the next prednisone dosage by utilizing the characterization assigned to the prednisone dosage criterion and the patient's current prednisone dosage. If the prednisone dosage is characterized as being "high," then the next prednisone dosage will be the current prednisone dosage less 5 milligrams. If the prednisone dosage is characterized as being "low," the next prednisone dosage will be the current prednisone dosage less 2.5 milligrams. If the prednisone dosage is characterized as "OK," the next prednisone dosage will be the same as the current prednisone dosage.

The final steps of FIG. 8A are to administer a next dose of Cyclosporin, RPM or FK 506 to the patient in accordance with the next dosage determined by the expert system, step 23 of FIG. 8A, and to administer a next dose of prednisone, if applicable, to the patient in accordance with the prednisone instruction (and the next prednisone dosage, if one is determined) from the expert system, step 171 of FIG. 8A.

If the response to the question in step 10 of FIG. 8 is that the Cyclosporin, RPM or FK 506 dosage instruction does not require an increase (i.e., it requires a decrease), or remains the same then the next steps of the combined embodiment of the present invention are the steps depicted in FIG. 8B, step 12 of FIG. 8. Those steps begin with delivering the patient's current dosage to the expert system, step 21 of FIG. 8B. The expert system receives the patient's current dosage through an expert computer program routine. Thereafter, through another expert computer routine, the expert system uses the rules provided in FIG. 13 together with the patient's current dosage and the characterization assigned to the Cyclosporin, RPM or FK 506 whole blood criterion to determine the patient's next dosage. The next dosage is then output to the monitor, via another expert computer routine, so the physician user can receive the next dosage from the expert system, step 22 of FIG. 8B. These two steps are essentially the same as steps 21 and 22 of the embodiment depicted in FIG. 3.

The next two steps of the process depicted in FIG. 8B requires the physician user to deliver the current prednisone dosage to the expert system, step 161 of FIG. 8B, if appropriate, and then receive the next prednisone dosage, step 162 of FIG. 8B, if applicable. These steps are the same as steps 161 and 162 of FIG. 8A. The final steps of FIG. 8B are to administer a next Cyclosporin, RPM or FK 506 dose to the patient in accordance with the next dosage determined by the expert system, step 23 of FIG. 8A, and to administer a next dose of prednisone, if applicable, to the patient in accordance with the prednisone instruction (and the next prednisone dosage, if one is determined) from the expert system, step 171 of FIG. 8A.

It should be noted that step 10 of the combined embodiment is only necessary because that embodiment utilizes steps from the embodiment depicted in FIG. 3, an embodiment which can only determine the next dosage when the next dosage is being decreased with respect to the current dosage. Step 10 is not absolutely necessary and the steps depicted in FIG. 8A could be used alone to determine the proper next dosage. This is the case regardless of whether the dosage is being increased or decreased. Hence, one implementation of this combined embodiment could use the steps depicted in FIG. 8A by itself without the steps of FIG. 8B.

Another implementation of the combined embodiment could substitute steps 14 and 18 of FIG. 4 with steps 21 and 22 of FIG. 8B to provide an implementation in which a modified FIG. 8B could be used by itself to determine the appropriate next dosage, no matter whether the next dosage is being increased or decreased. Such an implementation would not require the steps of FIG. 8A.

Once the steps contained in FIG. 8A, FIG. 8B or FIG. 8C have been completed, the next step encountered in the combined embodiment is that of step 24 of FIG. 8. (Reference numbers 27, 28 and 29 of FIGS. 8, 8A, 8B and 8C, denote these loop backs.) Step 24 queries whether a change in dosage is necessary. This step is the same as step 24 of FIGS. 5, 6 and 7.

If the answer to step 24 is "no", the patient receives the same Cyclosporin, RPM or FK 506 dosage (and prednisone dosage, if being administered), step 25 of FIG. 8, as the patient previously received; thereafter, step 24 of FIG. 8 is repeated. If the answer to the question contained in step 24 of FIG. 8 is "yes", then certain steps of the combined embodiment are repeated, i.e., step 3 of FIG. 8 and the steps thereafter.

Because in the preferred embodiment the patient receives a dosage of Cyclosporin, RPM or FK 506 every day after he or she begins treatment for the remainder of his or her life, step 24 of the embodiment depicted in FIG. 8 should be encountered everyday. In the preferred embodiment, the response to step 24 of FIG. 8 should be "yes" in the situations described above with respect to step 24 of FIGS. 5, 6 and 7. Step 24 of FIG. 8 assures that a patient receives a dosage every day and that dosage is reassessed in a systematic manner throughout the remainder of the patient's life.

I claim:

1. A method for treating a patient to prevent an adverse immune response by partially suppressing the patient's immune system without unduly suppressing the ability of the immune system to combat infection, comprising the step of:

(a) administering an initial dose of an immunosuppressant to the patient;

(b) examining the patient to determine information concerning patient examination criteria, wherein the patient examination criteria comprises toxicity and a blood level of the immunosuppressant;

(c) assigning a characterization to each of the patient examination criteria, each such characterization being selected from a predetermined standardized range of characterizations applicable to each patient examination criterion;

(d) providing the assigned characterizations to a computing device comprising:

a knowledge base comprising rules which include one of a plurality of treatment instructions in response to at least one of various combinations of the characterizations which can be assigned to the patient examination criteria, and an expert computer program including a first routine for prompting, through an output means, a user to enter, through an input means, the assigned characterizations; a second routine for selecting a treatment instruction by locating a rule which covers the assigned characterizations, and thereby determines the treatment instruction; and a third routine for communicating the treatment instruction to the output means;

(e) receiving from the computing device the treatment instruction; and (f) administering a next dose of the immunosuppressant to the patient in accordance with the treatment instruction.

2. A method according to claim 1, which comprises the method comprising the additional steps, after step (e) and before step (f), of:

(g) providing to the computing device data relating to a next immunosuppressant dosage determination, when the treatment instruction requires that the dosage be changed; and (h) receiving from the computing device the next immunosuppressant dosage, if one is determined;

wherein the expert computer program comprises a fourth routine for determining a next immunosuppressant dosage to be administered to the patient;

wherein the expert computer program contains at least one additional routine for receiving the data through the input means and communicating the next immunosuppressant dosage to the output means; and wherein the next immunosuppressant dose administered to the patient is determined in accordance with the treatment instruction, and the next immunosuppressant dosage, if one is determined.

3. A method according to claim 2, wherein the patient is selected from the group consisting of heart and kidney transplant patients and the patient examination criteria further comprises a rejection criterion.

4. A method according to claim 2, wherein the patient is a liver transplant patient and the patient examination criteria further comprise a rejection criterion, a creatinine level criterion, a bilirubin level criterion, and a SGOT and SGPT levels criterion.

5. A method according to claim 2, wherein the patient is afflicted with an autoimmune disease and the patient examination criteria further comprises a desired effect criterion.

6. A method according to claim 2, wherein the blood level is the blood plasma level of the immunosuppressant in the blood of the patient.

7. A method according to claim 2, wherein the blood level is the whole blood level of the immunosuppressant in the blood of the patient.

8. A method according to claim 2, wherein steps (b) through (h) are systematically repeated throughout the remainder of the patient's life.

9. A method according to claim 1, wherein the patient is an organ transplant recipient and steps (b) through (f) are repeated every day for the first two weeks after the patient has been administered the initial dose of the immunosuppressant, then twice a week for the next two weeks, then weekly for the next two months, and then monthly for the rest of the patient's life.

10. A method according to claim 2, wherein the patient is an organ transplant recipient and steps (b) through (h) are repeated every day for the first two weeks after the patient has been administered the initial dose of the immunosuppressant, then twice a week for the next two weeks, then weekly for the next two months, and then monthly for the rest of the patient's life.

11. A method according to claim 1, wherein the patient is afflicted with an autoimmune disease and steps (b) through (f) are repeated twice a week for the first two weeks after the patient has been administered the initial dose of the immunosuppressant, then weekly for the next month, and then monthly for the rest of the patient's life.

12. A method according to claim 2, wherein the patient is afflicted with an autoimmune disease and steps (b) through (h) are repeated twice a week for the first two weeks after the patient has been administered the initial dose of the immunosuppressant, then weekly for the next month, and then monthly for the rest of the patient's life.

13. A method according to claim 7, wherein the immunosuppressant is Cyclosporin and wherein the data comprises a current Cyclosporin dosage for the patient, a current Cyclosporin whole blood level for the patient and a desired Cyclosporin level for the patient; and wherein the fourth routine of the expert computer program determines the next Cyclosporin dosage by employing the following relationship:

$$ND = CD - (((((CL-DL)/CL)/(2.5+(CD/1500) \times 2.5))CD) + ((0.2 \times CD) \times (((1+d)-(1+e))/abs((1+d)))))$$

wherein,

ND = the patient's next Cyclosporin dosage,

CD = the patient's current Cyclosporin dosage,

CL = the patient's current Cyclosporin whole blood level, and

DL = the desired Cyclosporin level for the patient,

RD = the patient's previous Cyclosporin whole blood level e = CL - RD d = DL - RD.

14. A method according to claim 7 wherein the immunosuppressant is FK 506 and wherein the data comprise, the current FK 506 dosage for the patient, current FK 506 whole blood level for the patient and a desired FK 506 level for the patient; and wherein the fourth routine of the expert computer program determines the next FK 506 dosage by employing the following relationship:

$$ND = CD - (((((CL-DL)/CL)/(1+(CD/40)))/CD) + ((0.2 \times CD) \times (((1+d)-(1+e))/abs((1+d)))))$$

wherein,

ND = the next FK 506 dosage

CD=the patient's current FK 506 dosage,
CL=the patient's current FK 506 whole blood level,
DL=the desired FK 506 level for the patient,
RD=the patient's previous FK 506 whole blood level,
e=CL−RD, and
d=DL−RD.

15. A method according to claim 7 wherein the immunosuppressant is Rapamycin and wherein the data comprise, the current Rapamycin dosage for the patient, current Rapamycin whole blood level for the patient and a desired Rapamycin level for the patient; and wherein the fourth routine of the expert computer program determines the next Rapamycin dosage by employing the following relationship:

For RPM:

$$ND=CD-((((CL-DL)/CL)/(1+(CD/30)))/CD)+((0.2 \times CD) \times (((1+d)-(1+e))/abs((1+d))))$$

wherein
ND=the next RPM dosage,
CD=the patient's current RPM dosage,
CL=the patient's current RPM whole blood level,
DL=the desired RPM whole blood level for the patient,
RD=the patient's previous RPM whole blood level,
e=CL−RD, and
d=DL−RD.

16. A method according to claims 1, wherein the patient is also treated with a dosage of at least one additional immunosuppressant.

17. A method according to claim 16, wherein the additional immunosuppressant is prednisone.

18. A method according to claim 17, wherein the computing device provides a prednisone treatment instruction after (i) the patient has received an initial dose of prednisone, (ii) a prednisone dosage criterion is assigned a characterization from a predetermined range of standardized prednisone characterizations, and (iii) the characterization assigned to the prednisone dosage criterion is provided to the computing device in the first routine;

the prednisone treatment instruction being provided through means of a first prednisone treatment instruction routine which searches through a prednisone treatment knowledge base containing prednisone treatment rules until a prednisone treatment rule is found which covers the characterizations assigned to an efficacy criterion and the prednisone dosage criterion, and thereby determines the prednisone treatment instruction; and a second prednisone treatment routine for communicating the prednisone treatment instruction to the output means;

wherein the prednisone treatment instruction rules include one of a plurality of prednisone treatment instructions in response to at least one of various combinations of characterizations which can be assigned to the efficacy criterion and the prednisone dosage criterion.

19. A method according to claim 18, wherein the patient is the recipient of a transplanted organ and the efficacy criterion is a rejection criterion.

20. A method according to claim 18, wherein the patient is afflicted with an autoimmune disease and the efficacy criterion is a desired effect criterion.

21. A method according to claim 18, wherein the computing device provides a next prednisone dosage, if a decrease in the prednisone dosage is required by the prednisone treatment instruction.

22. A method according to claim 1, wherein the computing device determines at least one characterization to be assigned to a toxicity criterion through means of additional expert computer program routines comprising: a first routine for receiving characterizations assigned to toxicity determination criteria; a second routine which searches through a toxicity determination knowledge base containing toxicity determination rules until a toxicity determination rule is found which covers the toxicity determination characterizations assigned to the toxicity determination criteria, and thereby determines at least one characterization to be assigned to the toxicity criterion; and a third routine for communicating to the output means the characterization to be assigned to the toxicity criterion;

wherein the toxicity determination rules include at least one of the characterizations which can be assigned to the toxicity criterion in response to at least one of various combinations of the characterizations which can be assigned to the toxicity determination criteria.

23. A method according to claim 22, wherein the toxicity determination criteria comprise a tingling/loss of sensation toxicity determination criterion, a tremor toxicity determination criterion, a trouble sleeping toxicity determination criterion, a diabetogenicity toxicity determination criterion, and a change in creatinine level toxicity determination criterion.

24. A method for treating a patient to prevent an adverse immune response by partially suppressing the patient's immune system without unduly suppressing the ability of the immune system to combat infection, comprising the steps of:

(a) administering an initial dose of an immunosuppressant to the patient;

(b) examining the patient to determine a current immunosuppressant whole blood level for the patient;

(c) assigning a characterization to the patient's current immunosuppressant whole blood level from a predetermined standardized range of characterizations;

(d) providing the patient's current immunosuppressant dosage and the characterization assigned to the patient's current immunosuppressant whole blood level to a computing device comprising:

a knowledge base comprising rules which include one of a finite number of values for a decreased next immunosuppressant dosage in response to at least one of various combinations of characterizations which can be assigned to the patient's current immunosuppressant whole blood level and values for the patient's current immunosuppressant dosage; and an expert computer program including a first routine for prompting, through an output means, a user to enter, through an input means, the patient's current dosage and the characterization assigned to the patient's current immunosuppressant whole blood level; a second routine for selecting the next immunosuppressant dosage by locating the rule which covers the patient's current immunosuppressant dosage and the characterization assigned to the patient's current immunosuppressant whole blood level, and thereby determines the decreased next immunosuppressant dosage; and a third routine for communicating the decreased next immunosuppressant dosage to the output means;

(e) receiving from the computing device the decreased next immunosuppressant dosage; and (f) administering a next immunosuppressant dose in accordance with the decreased next immunosuppressant dosage determined by the computing device.

25. A method according to claim 24, wherein the immunosuppressant is FK 506.

26. A method according to claim 24, wherein the immunosuppressant is Rapamycin.

27. A method according to claim 24, wherein the immunosuppressant is Cyclosporin.

28. A method according to claim 24, wherein the patient is also treated with a dosage of at least one additional immunosuppressant agent.

29. A method according to claim 28, wherein the immunosuppressant agent is prednisone.

30. A method for treating a patient to prevent an adverse immune response by partially suppressing the patient's immune system without unduly suppressing the ability of the immune system to combat infection, comprising the steps of:

(a) administering an initial dose of FK 506 to the patient;

(b) examining the patient to determine a current FK 506 whole blood level for the patient;

(c) determining a desired FK 506 level for the patient;

(d) employing the following relationship along with the patient's current FK 506 dosage, the patient's current FK 506 whole blood level, and the desired FK 506 level for the patient to determine a next FK 506 dosage:

$$ND=CD-(((((CL-DL)/CL)(1+(CD/40)))/CD)+((0.2 \times CD) \times (((1+d)-(1+e))/abs((1+d)))))$$

wherein

ND=the next FK 506 dosage

CD=the patient's current FK 506 dosage,

CL=the patient's current FK 506 whole blood level,

DL=the desired FK 506 level for the patient,

RD=the patient's previous FK 506 whole blood level e=CL−RD d=DL−RD (e) administering a next dose of FK 506 to the patient in accordance with the next FK 506 dosage determined from the relationship.

31. A method for treating a patient to prevent an adverse immune response by partially suppressing the patient's immune system without unduly suppressing the ability of the immune system to combat infection, comprising the steps of:

(a) administering an initial dose of Rapamycin to the patient;

(b) examining the patient to determine a current Rapamycin whole blood level for the patient;

(c) determining a desired Rapamycin level for the patient;

(d) employing the following relationship along with the patient's current Rapamycin dosage, the patient's current Rapamycin whole blood level, and the desired Rapamycin level for the patient to determine a next Rapamycin dosage:

$$ND=CD-(((((CL-DL)/CL)(1+(CD/30)))/CD)+((0.2 \times CD) \times (((1+d)-(1+e))/abs((1+d)))))$$

wherein,

ND=the next RPM dosage,

CD=the patient's current RPM dosage,

CL=the patient's current RPM whole blood level,

DL=the desired RPM whole blood level for the patient,

RD=the patient's previous RPM whole blood level, e=CL−RD, and d=DL−RD.

(e) administering a next dose of Rapamycin to the patient in accordance with the next Rapamycin dosage determined from the relationship.

32. A method for treating a patient to prevent an adverse immune response by partially suppressing the patient's immune system without unduly suppressing the ability of the system to combat infection, comprising the steps of:

(a) administering an initial dose of Cyclosporin to the patient;

(b) examining the patient to determine a current Cyclosporin whole blood level for the patient;

(c) determining a desired Cyclosporin level for the patient;

(d) employing the following relationship along with the patient's current Cyclosporin dosage, the patient's current Cyclosporin whole blood level, and a potential next Cyclosporin dosage to determine a next Cyclosporin dosage:

$$ND=CD-(((((CL-DL)/CL)(2.5+(CD/1500) \times 2.5))/CD)+((0.2 \times CD) \times (((1+d)-(1+e))/abs((1+d)))))$$

wherein,

ND=the patient's next Cyclosporin dosage,

CD=the patient's current Cyclosporin dosage,

CL=the patient's current Cyclosporin whole blood level, and

DL=the desired Cyclosporin level for the patient,

RD=the patient's previous Cyclosporin whole blood level e=CL−RD d=DL−RD (e) administering a next dose of Cyclosporin to the patient in accordance with the next Cyclosporin dosage determined from the relationship.

\* \* \* \* \*